(12) United States Patent
Ikeda et al.

(10) Patent No.: US 11,406,982 B2
(45) Date of Patent: Aug. 9, 2022

(54) REAGENT KIT, METHOD FOR PRODUCTION OF REAGENT KIT, AND METHOD OF ASSOCIATING MEASUREMENT RESULTS

(71) Applicant: SYSMEX CORPORATION, Kobe (JP)

(72) Inventors: Koji Ikeda, Kobe (JP); Hiroyuki Fujino, Kobe (JP); Mieko Asada, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 486 days.

(21) Appl. No.: 16/204,473

(22) Filed: Nov. 29, 2018

(65) Prior Publication Data

US 2019/0160467 A1 May 30, 2019

(30) Foreign Application Priority Data

Nov. 30, 2017 (JP) .............................. JP2017-231147

(51) Int. Cl.
| | |
|---|---|
| *B01L 3/00* | (2006.01) |
| *G16H 40/63* | (2018.01) |
| *G16H 10/40* | (2018.01) |
| *G16H 40/40* | (2018.01) |

(52) U.S. Cl.
CPC ................ *B01L 3/52* (2013.01); *G16H 10/40* (2018.01); *G16H 40/40* (2018.01); *G16H 40/63* (2018.01); *B01L 2300/021* (2013.01)

(58) Field of Classification Search
CPC ..... B01L 3/52; B01L 2300/021; G16H 10/40; G16H 40/40; G16H 40/63
See application file for complete search history.

(56) References Cited

U.S. PATENT DOCUMENTS

| | | |
|---|---|---|
| 5,692,640 A | 12/1997 | Caulfield et al. |
| 2001/0039502 A1 | 11/2001 | Case |
| 2002/0009395 A1 | 1/2002 | Hirono et al. |

(Continued)

FOREIGN PATENT DOCUMENTS

| | | |
|---|---|---|
| CN | 1483172 A | 3/2004 |
| JP | H01-160360 U | 11/1989 |

(Continued)

OTHER PUBLICATIONS

Extended European search report dated Mar. 1, 2019 in a counterpart European patent application No. 18208260.2.

(Continued)

*Primary Examiner* — Jennifer Wecker
*Assistant Examiner* — Oyeleye Alexander Alabi
(74) *Attorney, Agent, or Firm* — Crowell & Moring LLP

(57) ABSTRACT

A reagent kit in which a brief measurement result is readily associated with subject information by suppressing erroneous input without using an integrated management system. This reagent kit 100 includes a container 10 used for measuring a sample by the sample measuring apparatus 300, a first identification label 30 including first identification information 31 associated with the measurement result 51 of the sample, and a second identification label 40 including second identification information 41 associated with the first identification information 31.

18 Claims, 26 Drawing Sheets

(56) References Cited

U.S. PATENT DOCUMENTS

| | | | | |
|---|---|---|---|---|
| 2003/0183683 | A1* | 10/2003 | Stewart | G16H 10/40 235/376 |
| 2005/0177129 | A1 | 8/2005 | Pacha et al. | |
| 2005/0246202 | A1* | 11/2005 | Hyoudou | G16H 10/60 705/3 |
| 2006/0275852 | A1 | 12/2006 | Montagu et al. | |
| 2007/0077655 | A1 | 4/2007 | Unger et al. | |
| 2008/0217391 | A1* | 9/2008 | Roof | G16H 10/40 235/375 |
| 2014/0100791 | A1* | 4/2014 | Darmstadt | G01N 35/00732 702/19 |
| 2014/0220585 | A1 | 8/2014 | Morhet et al. | |
| 2016/0054342 | A1 | 2/2016 | Son et al. | |
| 2018/0122508 | A1* | 5/2018 | Wilde | G16H 50/20 |
| 2019/0059861 | A1* | 2/2019 | Lough | A61B 42/40 |

FOREIGN PATENT DOCUMENTS

| | | | | |
|---|---|---|---|---|
| JP | 2002-024381 | A | | 1/2002 |
| JP | 2002-156317 | A | | 5/2002 |
| JP | 2004-028735 | A | | 1/2004 |
| JP | 2005-182507 | A | | 7/2005 |
| JP | 2006-317384 | A | | 11/2006 |
| JP | 2008-058349 | A | | 3/2008 |
| JP | 2008058349 | A | * | 3/2008 |
| JP | 2009-502685 | A | | 1/2009 |
| JP | 2009-175245 | A | | 8/2009 |
| JP | 2010-164516 | A | | 7/2010 |
| JP | 2011-503686 | A | | 1/2011 |
| JP | 2012-522450 | A | | 9/2012 |
| JP | 2014-066607 | A | | 4/2014 |
| JP | 2015-222198 | A | | 12/2015 |
| JP | 6157530 | B2 | | 7/2017 |
| WO | WO2014-092005 | A1 | | 6/2014 |
| WO | WO-2017062892 | A1 | * | 4/2017 ............... G01N 1/28 |

OTHER PUBLICATIONS

Diagramm Halbach Healthcare: "AG Patientenidentifikation im Projekt e-medPPP—Ergebnisse und Empfehlungen", Jul. 29, 2011, Retrieved from the Internet: URL:https://www.pro-patientensicherheit. de/fileadmin/Medienablage/Neue_Webseiten/Pro_Patientensicherheit/ Patientenidentifikation/110729_-_AG_Patientenidentifikation_-_e-medPPP_V_1.0.pdf [Retrieved on Dec. 16, 2019].

Typenex Medical: "Blood Bands", Nov. 4, 2014, Retrieved from the Internet: URL:https://web.archive.org/web/20141104141520/https:// www.typenex.com/products/blood-bands/ [Retrieved on Dec. 16, 2019].

Joint United Kingdom (UK) Blood Transfusion and Tissue Transplantation Services Professional Advisory Committee: "23.4: Donation identification numbers (DIN)", Jun. 28, 2017, Retrieved From the Internet: URL:https://web.archive.org/web/20170628131830/ https://www.transfusionguidelines.org/red-book/chapter-23-specification-for-the-uniform-labelling-of-blood-blood-components-and-blood-donor-samples/23-4-donation-identification-numbers-din [Retrieved on Dec. 16, 2019].

Brenmoor, Products catalogs, Apr. 6, 2016, Retrieved from the Internet: URL:https://cdn.aumet.me/productscatalogs/9b1388c7-2126-4937-aba1-87be6aa0a2f6.pdf [Retrieved on Dec. 16, 2019].

Communication pursuant to Article 94(3) EPC dated Jul. 27, 2020 in a counterpart European patent application No. 18208260.2.

Chinese Office Action dated Apr. 30, 2021 in a counterpart Chinese patent application No. 201811420738.8.

Communication pursuant to Article 94(3) EPC dated Apr. 20, 2021 in a counterpart European patent application No. 18208260.2.

Japanese Office Action dated Oct. 12, 2021 in a counterpart Japanese patent application No. 2018-160552.

Summons to attend oral proceedings pursuant to Rule 115(1) EPC issued on Dec. 2, 2021 in a counterpart European patent application No. 18208260.2.

Chinese Office Action dated Dec. 8, 2021 in a counterpart Chinese patent application No. 201811420738.8.

Japanese Office Action dated Jun. 29, 2021 in a counterpart Japanese patent application No. 2018-160552.

Decision of Refusal dated Mar. 15, 2022 in a counterpart Japanese patent application No. 2018-160552.

* cited by examiner

REAGENT KIT, METHOD FOR PRODUCTION OF REAGENT KIT, AND METHOD OF ASSOCIATING MEASUREMENT RESULTS

RELATED APPLICATIONS

This application claims priority from prior JP Patent Application No. 2017-231147, filed on Nov. 30, 2017, entitled "REAGENT KIT, METHOD FOR PRODUCTION OF REAGENT KIT, AND METHOD OF ASSOCIATING MEASUREMENT RESULTS", the entire contents of which are incorporated herein by reference.

BACKGROUND OF THE INVENTION

1. Field of the Invention

The present invention relates to a reagent kit used in a sample measuring apparatus for measuring a sample (for example, refer to Patent Document 1).

2. Description of the Related Art

US Patent Application Publication No. 2016/0054342, as shown in FIG. 40, discloses that sample measurement is performed using a disc-shaped cartridge 905 by a sample measuring apparatus 900. The sample measuring apparatus 900 includes a display screen 901, and a loader 902 provided with a placement unit 903 in which the cartridge 905 is placed. The display screen 901 has a touch panel, and can accept operation input through a user interface screen that includes a button 904. Information such as ID, race, sex, age, height, weight, and the like of the subject is input through the user interface screen. The user places the cartridge 905 into which the blood sample is injected in the placement unit 903, sends the loader 902 into the device, and then operates the button 904 displayed on the display screen 901. Upon receiving the input of the button 904, the sample measuring apparatus 900 starts the measurement operation of the sample using the cartridge 905.

SUMMARY OF THE INVENTION

The sample measuring apparatus disclosed in US Patent Application Publication No. 2016/0054342 is a small measuring apparatus for so-called PoC (point of care) examination. Unlike a large-scale medical facility that integrally manages patient information and measurement results by an electronic medical chart system, a sample measuring apparatus for PoC is mainly used in small clinics and the like which do not have an integrated management system working in concert with the measuring apparatus. Therefore, the sample measuring apparatus for PoC preferably should be able to associate and manage the measurement result of the sample and the subject information of the subject from which the sample was collected without using an integrated management system.

When a physician conducts examinations of a subject, it is preferable that the PoC sample measuring apparatus instantaneously measures the collected sample and immediately confirms the result of the examination on the spot so that the subject can feel close to the examination.

In US Patent Application Publication No. 2016/0054342, the information input operation becomes complicated since it is necessary for the user to manually input detailed information such as the ID of the subject on a small user interface screen. Erroneous operation is likely to occur in methods in which the user performs manual inputs on a small user interface screen, and there is a possibility of misinterpretation of measurement results due to ID input errors. The operations on the small user interface screen also is necessary when confirming the examination result, so inconvenience may be caused by erroneous operation on the small user interface screen for the subject who wishes to immediately confirm the examination result on the spot. That is, with a conventional sample measuring apparatus for PoC, manual operations are cumbersome and required and are likely to cause erroneous operation when starting a sample measurement since operations on a small user interface screen are necessary with miniaturization. As a result, there are cases where the measurement result is misinterpreted due to erroneous input, a result is associated with an erroneous subject, or a case where the measurement result of the subject cannot be confirmed due to erroneous input.

The present invention is directed at suppressing erroneous inputs so that measurement results can be easily associated with subject information without using an integrated management system.

A reagent kit (100) according to a first aspect of the present invention includes a container (10) used for measuring a sample by a sample measuring apparatus (300), a first identification label 30 including first identification information (31) associated with a measurement result (51) of a sample, and a second identification label (40) including second identification information (41) associated with the first identification information (31). Note that the association is to take one-to-one correspondence. The first identification label (30) also is a broad concept that includes not only labels adhered or installed to the surface of an object, but also labels printed or stamped on the surface of an object.

The first identification information (31) of the first identification label (30) is associated with the measurement result (51) when a sample is measured using the container (10) by providing the first identification label (30) in the reagent kit (100) according to the first aspect. The first identification information (31) associated with the measurement result (51) and the second identification information (41) of the second identification label (40) are associated in advance by providing the second identification label (40). Therefore, even if used in a small-scale clinic or the like which does not have an integrated management system for managing patient information and measurement results, the user can associate the subject information with the information of the measurement result (51) of the subject based on the second identification information (41) and the first identification information (31). Since the first identification label (30) and the second identification label (40) are included in the reagent kit (100) beforehand, there is no need for the user to manually input the subject information to the sample measuring apparatus every time the user performs a sample measurement, and it is not necessary to manually associate the first identification information (31) given to the measurement result (51) with the second identification information (41) attached to the recorded item of the subject information. When confirming a measurement result (51), the measurement result (51) which has the first identification information (31) associated with the second identification information (41) can be confirmed without manual input of the measurement result (51) by using the second identification information (41). As a result, it is possible to suppress erroneous input and easily associate the measurement result with the subject information without using an integrated management system.

In the reagent kit (100) according to the first aspect, the first identification label (30) includes first identification information (31) that can be read by the sample measuring apparatus (300), and the second identification label (40) is provided so as to be attachable to the recorded item of subject information. With this configuration, the read first identification information (31) is associated with the measurement result (51) by reading the first identification information (31) from the first identification label (30) at the time of measurement by the sample measuring apparatus (300). The user also can attach the second identification label (40) to the recorded item of the subject information such as the chart of the subject from whom the sample was collected. As a result, the association between the subject information based on the second identification information (41) and the first identification information (31) and the information on the measurement result (51) can be performed more easily.

In the reagent kit (100) according to the first aspect, preferably, the first identification information (31) includes information (71) for identifying the container (10). The information (71) for identifying the container (10) is information that uniquely identifies the container (10), such as the ID of the container (10), for example. With this configuration, not only the measurement result (51) and the subject information are associated with each other by the first identification information (31), but the container (10) used for generating the measurement result (51) also can be specified by the information (71) for identifying the container (10). Information (71) for identifying the container (10) at the start of the measurement is read by the sample measuring apparatus (300), for example, so as to avoid the use of a container other than the genuine product, specifying the reuse of a used container, or performing an inappropriate measurement.

In the reagent kit (100) according to the first aspect, preferably, the first identification label (30) includes information (72) relating to measurements using the container (10). With this configuration, information necessary for a measurement can be acquired from the first identification label (30). For example, the information (72) relating to a measurement using the container (10) is read by the sample measurement device (300) at the start of the measurement, so that the type of the container (10) is grasped and the sample measurement apparatus (300) can perform the measurement operation according to the type of container (10).

In this case, the information (72) relating to the measurement using the container (10) preferably includes information of at least one among the measurement condition, the measurement item, and the calibration curve (77). With this configuration, it is possible for the sample measurement apparatus (300) to perform an appropriate measurement operation according to the information of the measurement condition and the measurement item information, without separately inputting information by manual input by the user. According to the information on the calibration curve (77), it is possible to carry out the measurement with high accuracy without preparing a calibration curve by a separate operation of the user.

In the reagent kit (100) according to the first aspect, the second identification information (41) preferably includes the same or corresponding information as the first identification information (31). Here, the corresponding information is information different from the first identification information (31) but has a one-to-one correspondence to the first identification information (31). With this configuration, it is possible to associate the second identification information (41) with the first identification information (31) easily and reliably.

In this case, the second identification information (41) preferably includes the same encrypted information as the first identification information (31). According to this configuration, reading by a third party other than the user can be suppressed since the first identification information (31) and the second identification information (41) are encrypted. Then, for example, only the user can manage the subject information and the measurement result (51) in association with each other by making it possible to decrypt using the information managed by the user.

In the configuration in which the second identification information (41) includes the same information or corresponding information to the first identification information (31), the first identification information (31) preferably includes information that the second identification information (41) was converted by a predetermined method. Here, conversion by a predetermined method includes changing the second identification information (41) to other information by a predetermined method, and includes calculation of a hash value by a predetermined hash function. With this configuration, it is possible to verify the first identification information (31) associated with the measurement result (51) with the corresponding second identification information (41) by reverse conversion of the first identification information (31) by a predetermined method and restoring to the second identification information (41), or conversion of the second identification information (41) by a predetermined method to obtain the first identification information (31). A third party who does not know the conversion method can be prevented from verifying the first identification information (31) and the corresponding second identification information (41).

In the reagent kit (100) according to the first aspect, the first identification label (30) preferably is provided on/in the container (10). With this configuration, for example, when setting the container (10) in the sample measuring apparatus (300), the first identification information (31) can be directly read from the first identification label (30) provided in the container (10). As a result, it is possible to omit the work of the user attaching the first identification label (30) to the container (10).

In the reagent kit (100) according to the first aspect, the container (10) preferably has a housing part (11) for accommodating a reagent that reacts with the sample, and a housing body (20) for accommodating the container (10). With this configuration, even when a reagent is contained in the container (10), the container (10) is shielded or sealed by the housing body (20) and maintains a state suitable for storage of the reagent.

In the reagent kit (100) according to the first aspect, the first identification label (30) is separably provided in the housing body (20), or is housed inside the housing body (20) together with the container (10).

In the reagent kit (100) according to the first aspect, the second identification label (40) preferably is separably provided in either the container (10) and the housing body (20), or the container 10) are accommodated inside the housing body (20) together with the container (10). With such a configuration, the user can easily take out the second identification label (40) from the reagent kit (100) and easily attach it to the recorded item of the subject information such as a medical record.

In the reagent kit (100) according to the first aspect, the second identification label (40) preferably is a label provided so as to be attachable to the object. With this configuration, unlike, for example, a type of label that cannot be pasted, the second identification label (40) can be easily fixed to subject information such as a medical record.

In this case, it is preferable that the second identification label (40) is provided so as to be superimposed on the first identification label (30) in a state where it can be separated from the first identification label (30). With this configuration, when the second identification label (40) is superimposed over the first identification label (30), the user can peel off the second identification label (40) and add it to the subject information such as a medical record.

The reagent kit (100) according to the first aspect preferably further comprises a housing body (20) that houses the container (10), wherein the first identification label (30) and the second identification label (40) are also attached to the housing body (20). Here, the term "attached" is a broad concept that includes not only attached to an object by adhesion or the like, but also attached by being sandwiched between an object and a fixed sheet adhered to the object. With this configuration, the user can easily recognize the presence of the first identification label (30) and the second identification label (40) by being attached to the housing body (20). Furthermore, as compared with the case where the second identification label (40) is attached to the container (10), the second identification label (40) can be easily separated and attached to subject information such as a medical record.

In the reagent kit (100) according to the first aspect, it is preferable that the first identification label (30) and the second identification label (40) are all attached to the container (10). With this configuration, when the container (10) is used, the user can reliably recognize the presence of the first identification label (30) and the second identification label (40). It is possible to omit the work for the user to paste the first identification label (30) on the container (10).

The reagent kit (100) according to the first aspect preferably includes a housing body (20) that houses the container (10), the first identification label (30) is attached to the container (10), and the second identification label (40) is attached to the housing body (20). With such a configuration, since the first identification label (30) is attached to the container (10) in advance, it is possible to omit the work of the user attaching the first identification label (30) to the container (10) and the like. Since the second identification label (40) is attached to the housing body (20), it is easy to separate the second identification label (40) as compared with the case where the second identification label (40) is attached to the container (10), and it then can be attached to subject information.

The reagent kit (100) according to the first aspect preferably includes a housing body (20) for containing the container (10), wherein the housing body (20) has regulated unsealing position, the second identification label (40) is provided in the housing body (20) so as to overlay the unsealing position, and when the housing body (20) is opened, the second identification label (40) is separated from the housing body (20), or the housing body (20) can be opened by separating the second identification label (40) from the housing body (20). With this configuration, when the user unseals the housing body (20), the second identification label (40) is reliably separated and can be attached to subject information such as a medical record.

In the reagent kit (100) according to the first aspect, it is preferable that the first identification information (31) and the second identification information (41) include the same text or figure, and the second identification label (40) displays text or graphic which are the second identification information (41) so as to be visually recognizable. With this configuration, since it is possible to visually recognize the correspondence relationship between the first identification information (31) and the second identification information (41), for example, when a user uses a plurality of reagent kits (100), the user can visually distinguish the second identification information (41) of each reagent kit (100) even in cases where sample measurements are to be performed on a plurality of subjects.

The reagent kit (100) according to the first aspect also includes a housing body (20) that preferably contains the container (10), and the second identification label (40) is separably provided on either a container (10) and the housing body (20) so that the appearance changes before and after separation. Here, the change in appearance before and after separation means that the appearance such as color, pattern, shape, or the like of the second identification label (40) changes by separation, for example. With this configuration, it is possible for the user to grasp at a glance that the second identification label (40) has been used due to a change in appearance. Therefore, even when a plurality of reagent kits (100) are used, it is possible for the user to visually distinguish the second identification information (41) of each reagent kit (100).

In the reagent kit (100) according to the first aspect, it is preferable that the first identification label (30) and the second identification label (40) have different shapes, colors or patterns so as to be visually distinguishable. With this configuration, the user can easily distinguish the first identification label (30) and the second identification label (40). Therefore, it is possible for the user to more certainly recognize which label should be attached to the subject information such as a medical record.

In the reagent kit (100) according to the first aspect, it is preferable that the first identification label (30) includes one of a bar code, a multidimensional code, and an RF tag. With this configuration, the sample measuring apparatus (300) can easily read the first identification information (31) without contact by optical reading or short-range wireless communication.

In the reagent kit (100) according to the first aspect, it is preferable that the second identification label (40) includes one of a bar code, a multidimensional code, and an RF tag. With this configuration, it is possible to read the second identification information (41) easily by optical reading or short range wireless communication.

The reagent kit (100) according to the first aspect preferably includes a housing body (20) for housing the container (10) and a third identification label (80) provided on the housing body (20), wherein the third identification label (80) is provided so as to be separable from the housing body (20) by unsealing the housing body (20), and the second identification label (40) is provided on the housing body (20) so as to be separable from the housing body (20) by unsealing the housing body (20). With this configuration, information on the third identification label (80) can be used when unused and before the unsealing of the housing body (20) the information of the second identification label (40) can be used after unsealing.

In this case, it is preferable that the third identification label (80) includes information (75a) indicating that it is before unsealing, and the second identification label (40) includes information (75b) indicating that it is unsealed. With this configuration, it is possible to reliably discriminate whether the reagent kit (100) is unopened or opened by the third identification label (80) and the second identification label (40). Therefore, it is possible to avoid reusing the used container (10) by mistake.

In the configuration also including the third identification label (80), it is preferable that the unseal position of the container (20) is regulated, and the third identification label (80) is attached so as to overlay the unseal position; the second identification label (40) is provided so that the second identification label (40) is exposed from the housing body (20) by unsealing the housing body (20). With this configuration, it is possible to expose the second identification label (40) while separating the third identification label (80) by unsealing the housing body (20), and avoid removing the second identification label (40) with the third identification label (80).

In the configuration also including the third identification label (80), and the third identification label (80) preferably includes at least one of information (71) for identifying the container (10), information relating to the quality of the container (76), and a calibration curve (77). In this way, when the information (71) for identifying the container (10) is included, the third identification label (80) can be used for inventory management or the like. When the information (76) on the quality of the container (10) is included, the third identification label (80) can be used for quality control and the like. In the case of including the calibration curve (77), it is possible to accurately perform the measurement using the calibration curve (77) of the third identification label (80) without separately preparing the calibration curve by user operation.

In the reagent kit (100) according to the first aspect, it is preferable that the second identification label (40) has an entry area (42) for entering information. With such a configuration, when measuring with the container (10), the user directly fills in the second identification label (40) with the measurement date and time of measurement, measurement items and the like, and then the second identification label (40) can be attached to subject information such as a chart. Therefore, it is possible to facilitate the management of the subject information and the measurement result (51).

In the reagent kit (100) according to the first aspect, it is preferable that the second identification label (40) includes information (78) for accessing the server (600) for managing the measurement result using the container (10). According to this configuration, the user can access the server (600) immediately by reading information from the second identification label (40) by storing the URL for accessing the server (600) in the second identification label (40), for example, as information (78) for accessing the server (600). Then, the measurement result data (50) recorded in the server (600) can be specified and acquired by using the second identification information (41) associated with the first identification information (31).

In the reagent kit (100) according to the first aspect, it is preferable that the housing body (20) accommodating the container (10) is also provided, and the container (20) is a bag. Here, when the reagent is contained in the container (10) in advance, it is desirable to control the storage environment such as contact with outside air, temperature, and humidity so that the reagent does not deteriorate. When packaging the housing body (20) into a bag, for example, by using a packaging bag having gas and moisture proofing properties, it is possible to reduce the packaging size as compared with a packaging box or the like, while suppressing deterioration of the container (10) during storage.

In the reagent kit (100) according to the first aspect described above, the container (10) may be either a cartridge, a well plate, or a tubular container.

A method of manufacturing a reagent kit according to a second aspect of the present invention is a method of manufacturing a reagent kit (100) used for measurement of a sample by a sample measuring apparatus (300), the method including housing in an openable housing body (20) a container (10) having a housing part (11) for housing reagent for reacting with a sample, affixing to the reagent kit (100) a first identification label (30) including first identification information (31) to be associated with the sample measurement result (51), and affixing to the reagent kit (100) a second identification label 40) including second identification information (41) associated with the first identification information (31) and provided so as to be affixed to a recorded item of the subject information.

In the method of manufacturing a container according to the second aspect, when a sample measurement is performed using the container (10), the first identification label (30) is associated with the measurement result (51) of the sample by attaching the first identification label (30) to the reagent kit (100). When performing a sample measurement using the container (10), the user can record the medical record of the subject whose sample is collected, and the second identification label (40) can be attached to the recorded item of the subject information by attaching the above-described second identification label (40) to the reagent kit (100). As a result, the subject information and the information of the measurement result (51) of the subject can be associated with each other based on the second identification information (41) and the first identification information (31). Further, it is not necessary for the user to manually input the subject information to the sample measuring apparatus every time the user performs a sample measurement, and association between the first identification information (31) applied to the measurement result (51) and the 2 identification information (41) applied to the subject information can be reliably performed. When confirming a measurement result (51), the measurement result (51) which has the first identification information (31) associated with the second identification information (41) can be confirmed without manual input of the measurement result (51) by using the second identification information (41). As a result, it is possible to suppress erroneous input and easily associate the measurement result with the subject information without using an integrated management system.

A data structure according to a third aspect of the present invention is a measurement result management data structure including first identification information (31) recorded in a first identification label (30) attached to a reagent kit (100) used for measurement of a sample by a sample measuring apparatus, and second identification information (41) recorded on the second identification label (40) attached to the reagent kit (100) and associated with the first identification information (31); wherein the sample measuring apparatus (300) generates measurement result data (50) associated with the first identification information (31) read from the first identification label (30) in the measurement result (50) of the sample using the container (10), stores the measurement result data (50) or transmits it to the server (600) managing the measurement result (51), the terminal (500) handling the information of the subject from whom the sample was collected stores the measurement result in at least one of the sample measuring apparatus (300) and the server (600) managing the measurement result (51) based on the second identification information (41) read from the second identification label (40), and specifies and acquires the measurement result data (50) including the first identification information (31) associated with the second identification information (41).

In the data structure according to the third aspect, the measurement result data (50) associated with the measurement result (51) and first identification information (31) are generated at the time of sample measurement using the container (10) by the first identification information (31) recorded on the first identification label (30), and stored in the sample measuring apparatus (300), or stored in the server (600) for managing the measurement result (51). Based on the second identification information (41) read from the second identification label (40), the terminal (500) specifies the measurement data (50) including the first identification information (31) associated with the second identification information (41) based on the second identification information (41) read from the second identification label (40), and acquires the measurement data (50) from the sample measuring apparatus (300) or the server (600) for managing the measurement results (51). As a result, when the user can associate the subject information and information of the measurement result (51) of the same subject based on the second identification information (41) and the first identification information (31) by applying the second identification label (40) to the recorded item of the subject information such as a chart of the subject from whom the sample was collected. It is not necessary for the user to manually input the subject information to the sample measuring apparatus every time a sample is measured, and the first identification information (31) associated with the measurement result (51) and the second identification information (41) applied to the subject information can be reliably associated. When confirming a measurement result (51), the measurement result (51) which has the first identification information (31) associated with the second identification information (41) can be confirmed without manual input of the measurement result (51) by using the second identification information (41). As a result, it is possible to suppress erroneous input and easily associate the measurement result with the subject information without using an integrated management system.

In the data structure according to the third aspect, it is preferable that at least one of the first identification information (31) and the second identification information (41) includes information for identifying the container (10), and the terminal (500) acquires the information of the container (10) used for generating the measurement result (51) from the first identification information (31) or the second identification information (41) included in the measurement result data (50). With this configuration, not only the measurement result (51) and the subject information are associated with each other by the first identification information (31), the container (10) used to generate the measurement result (51) is specified and the measurement result (51) and corresponding container (10) are managed.

In the data structure according to the third aspect, it is preferable that the first identification information (31) includes information on the reagent contained in the container (10), and the information of the calibration curve (77) for measuring the measurement result of a sample using the reagent is acquired from the server (650) for managing the reagent information based on the information of the reagent contained in the container (10). With this configuration, information on the calibration curve (77) can be specified based on the information on the reagent contained in the container (10) and acquired from the server (650) for managing the reagent information. As a result, an appropriate measurement result can be obtained without preparing a calibration curve for measurement. The calibration curve (77) also can be slightly changed depending on the elapsed period of time after the preparation of the reagent, so in the configuration that acquires the calibration curve (77) from the server (650) for managing the reagent information, highly accurate measurement can be achieved since information on the calibration curve (77) can also be updated.

A method of associating measurement results according to a fourth aspect of the present invention, includes measuring a sample, associating first identification information (31) with the measurement result (51) of the sample, attaching the identification label (40) including the second identification information (41) associated with the first identification information (31) to the recorded item of the subject information.

In the method of associating measurement results according to the fourth aspect, the first identification information (31) of the first identification label (30) is associated with the measurement result (51) of the sample at the time of sample measurement. The first identification information (31) associated with the measurement result (51) and the second identification information (41) of the second identification label (40) are associated beforehand by providing the identification label (40). Therefore, even if an integrated management system, the user can associate the subject information and the measurement result (51) of the subject based on the second identification information (41) and the first identification information (31). Since the second identification information (41) is included in the identification label (40) in advance, it is unnecessary for the user to manually enter the subject information into the sample measuring apparatus every time a sample is measured, and the association of the first identification information (31) applied to the measurement result (51) and the second identification information (41) attached to the recorded item of the subject information can be performed without manual input. When confirming a measurement result (51), the measurement result (51) which has the first identification information (31) associated with the second identification information (41) can be confirmed without manual input of the measurement result (51) by using the second identification information (41). As a result, it is possible to suppress erroneous input and easily associate the measurement result with the subject information without using an integrated management system.

It is possible to easily associate the measurement result with the subject information while suppressing erroneous input without using an integrated management system.

DETAILED DESCRIPTION OF THE PREFERRED EMBODIMENTS

Hereinafter, embodiments will be described with reference to the drawings.

First Embodiment

Summary of Reagent Kit

A summary of a reagent kit 100 according to this embodiment will be described with reference to FIG. 1.

Figure 1:
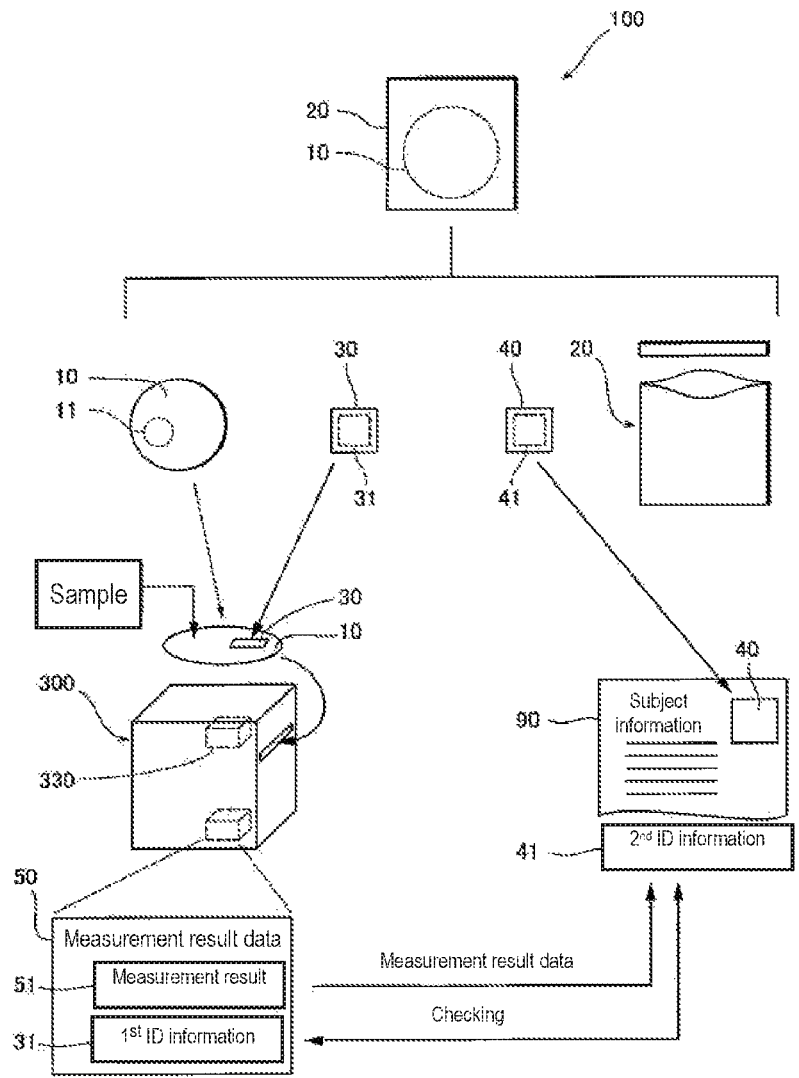
FIG. 1 is a schematic diagram of a reagent kit according to a first embodiment.

The reagent kit 100 shown in FIG. 1 is configured as a product including a container 10 used for measuring a sample by the sample measuring apparatus 300.

The container 10 is configured so that measurement of a sample can be performed simply by a small sample measuring apparatus 300 for PoC examination. That is, the container 10 is formed into a shape suitable for use with the sample measuring apparatus 300, and is set in the sample measuring apparatus 300.

The container 10 has a housing part 11 for containing a reagent that reacts with the sample. The container 10 has one or a plurality of housing parts 11 for containing reagents used for measurement of samples. A reagent may be stored in advance in the housing part 11, or a reagent may not be contained in the housing part 11. Reagents can be injected from the outside into the housing part 11 that does not contain a reagent. The housing part 11 may have a volume capable of accommodating a predetermined amount of liquid.

A sample collected from a subject is injected into the container 10. Mixing, stirring, warming or cooling of the sample and the reagent, movement of solid or liquid containing the sample, and various other operations can be performed inside the container 10 by the sample measuring apparatus 300.

The reagent in the container 10 reacts with the test substance in the sample to cause a change in the sample that is directly or indirectly measurable from the outside of the container 10. For example, the reagent emits light depending on the amount of the test substance. Luminescence is, for example, chemiluminescence or fluorescence. The reagent includes, for example, a labeling substance that specifically binds to the test substance. The labeling substance, for example, produces a signal that is measurable from outside the container 10. The labeling substance includes chemiluminescent substances or fluorescent substances, radioactive isotopes and the like. The reagent also may be one which develops color according to the amount of the test substance or one which causes turbidity depending on the amount of the test substance.

The measurement of the sample includes measuring the presence or absence of a test substance according to the measurement item, the amount or concentration of the test substance, and the size and shape of the sample in the case of a particulate sample. The type of reagent contained in the container 10 differs depending on the measurement item. There may be variations of multiple types of containers 10 for each measurement item. The container also may be a container 10 that can measure a plurality of different measurement items.

The container 10 is a replaceable consumable item. That is, when the container 10 is used for measurement for a preset number of times, it is discarded. The number of usable times of the container 10 is one or several times. The container 10 may take the form of, for example, a cartridge, a well plate, and a tubular container. A cartridge is a replaceable part that summarizes functions necessary for detecting a test substance contained in a sample. The well plate is a plate-like member formed with a well which is a recess capable of containing a liquid. A tubular container is a tubular container opened at one end and closed at the other end, for example, a cuvette, a test tube, a blood collection tube or the like. FIG. 1 shows an example in which the container 10 is a disk type disk-shaped cartridge.

The reagent kit 100 of the present embodiment includes a container 10, a first identification label 30, and a second identification label 40. In the example of FIG. 1, the container 10 is accommodated in the housing body 20. The container 10 is provided to the user in a state of being accommodated in the unsealable housing body 20. The reagent kit 100 also may not include the housing body 20.

The housing body 20 is a container in which an accommodation space for accommodating an object is formed. The housing body 20 accommodates at least the container 10 therein. The housing 20 is, for example, a box or a bag. The housing body 20 accommodates the container 10 therein and is provided to the user in a closed state in advance. The housing body 20 is unsealed when using the container 10, and the container 10 is taken out from within. When the reagent is stored in advance in the container 10, it is desirable to suppress deterioration of the reagent as much as possible. For example, the housing 20 houses the container 10 in a sealed state. In this way the container 10 can be isolated from the external atmosphere. For example, the housing body 20 may be made of a moisture-proof material. In this way the container 10 can be isolated from moisture even when exposed to a high humidity environment during transportation or the like. For example, the housing body 20 may be made of a heat insulating material. In this way it is possible to suppress the influence of temperature change during shipping.

The first identification label 30 is an information recording medium on which information is recorded in advance. The first identification information 31 is recorded in the first identification label 30. The first identification information 31 can be read by the sample measuring apparatus 300. The first identification information 31 is associated with the measurement result 51 of the sample. That is, the first identification label 30 is used for the sample measuring apparatus 300 together with the container 10. The first identification information 31 is information for identifying the measurement result 51 of the sample using the container 10. That is, as a result of performing a plurality of sample measurements by the sample measuring apparatus 300, the plurality of generated measurement results 51 can be distinguished from each other based on the first identification information 31.

The second identification label 40 is an information recording medium on which information is recorded in advance. The second identification information 41 is recorded in the second identification label 40. The second identification label 40 is provided so as to be attachable to the recorded item of the subject information. For example, the second identification label 40 is preliminarily separated from the housing body 20 and the container 10. For example, although the second identification label 40 is provided on the housing body 20 or the container 10, it can be separated. Therefore, when the user uses the container 10, the user can attach the second identification label 40 to the recorded item of the subject information such as the chart 90 of the subject from which the sample was taken.

The second identification information 41 is information associated with the first identification information 31. The second identification information 41 is associated one by one with the first identification information 31 of the same container 10. That is, when a plurality of measurement results 51 to which the first identification information 31 is attached are generated, each of the first identification information 31 is uniquely identified by the corresponding second identification information 41. Therefore, by using the second identification information 41 and the first identification information 31 of the specific reagent kit 100, it is possible to identify the measurement result 51 obtained by using the container 10 included in the set.

Both the first identification label 30 and the second identification label 40 are articles attached to the reagent kit 100. The first identification label 30 and the second identification label 40 may be accommodated in the housing body 20 together with the container 10. The first identification label 30 may be printed or engraved on the surface of the container 10.

When using the container 10, the user takes out the container 10 from the housing body 20, injects the sample collected from the subject into the container 10, and then sets the container 10 in the sample measuring apparatus 300. The user also causes the reading unit 330 of the sample measuring apparatus 300 to read the first identification information 31 from the first identification label 30. Then, the user starts the measurement operation by the sample measuring apparatus 300 using the container 10. On the other hand, the user attaches the second identification label 40 to the recorded item of the subject information from which the sample was collected. For example, the second identification label 40 is attached to the medical chart 90 which describes the subject information of the subject from whom the sample is collected.

Note that the first identification label 30 and the second identification label 40 may be a seal label having one side as an adhesive surface, or a card type label having no adhesive surface. In the card type configuration, the label can be fixed in a predetermined position by inserting it into a card slot, or by using a fixing device such as a stapler.

When the measurement by the sample measuring apparatus 300 is completed, the sample measuring apparatus 300 generates the measurement result data 50 including the measurement result 51 and the first identification information 31.

The first identification information 31 is previously associated with the second identification information 41 on a one-to-one basis. Therefore, the user uses the second identification information 41 recorded on the second identification label 40 attached to the medical record 90 or the like to specify and acquire the measurement result data 50 including the first identification information 31 associated with the second identification information 41. In this way the information of the subject described in the medical chart 90 to which the second identification label 40 is attached at the time of measuring the sample, and the measurement result 51 of the sample collected from the subject are uniquely associated and managed.

In this embodiment described above, even without using an integrated management system, the subject information and the measurement result 51 of the subject can be associated based on the second identification information 41 and the first identification information 31. Since the first identification label 30 and the second identification label 40 are included in the reagent kit 100 in advance, it is unnecessary for the user to manually enter the subject information into the sample measurement apparatus every time a sample is measured, and it is possible to reliably associate the first identification information 31 applied to the measurement result 51 with the second identification information 41 assigned to the subject information. As a result, it is possible to easily suppress the erroneous input and associate the measurement result 51 with the subject information without using an integrated management system.

Next, a method of associating measurement results will be described. The method of associating measurement results according to the present embodiment includes the following steps (1) to (3). (1) Measure the sample. (2) Associate the first identification information 31 with the measurement result 51 of the sample. (3) Attach the identification label 40 including the second identification information 41 associated with the first identification information 31 to the recorded item of the subject information.

(1) In the step of measuring a sample, a sample collected from a subject is injected into the container 10, and then the container 10 is set in the sample measuring apparatus 300. Then, the measurement operation using the container 10 is started by the sample measuring apparatus 300. As a result, the measurement result (51) is generated by the sample measuring apparatus 300.

(2) In the step of associating the first identification information 31 with the measurement result 51, for example, the first identification information 31 is read from the first identification label 30 by a reading unit 330 of the sample measuring apparatus 300. The read first identification information 31 is associated with the measurement result 51 by the sample measuring apparatus 300, and the measurement result data 50 including the measurement result 51 and the first identification information 31 are generated.

(3) In the step of attaching the identification label 40 to the recorded item of the subject information, the second identification label 40 is affixed to the recorded item of the chart 90 or the like in which the subject information of the subject from whom the sample is collected is described.

The first identification information 31 is previously associated with the second identification information 41 on a one-to-one basis. Therefore, the information of the subject described in the medical chart 90 to which the second identification label 40 is attached at the time of measuring the sample, and the measurement result 51 of the sample collected from the subject are uniquely associated by the user.

In this embodiment described above, even without using an integrated management system, the subject information and the measurement result 51 of the subject can be associated based on the second identification information 41 and the first identification information 31. Since the second identification information 41 is included in the identification label 40 in advance, there also is no need for the user to manually enter the subject information into the sample measuring apparatus every time the user performs a sample measurement. Also in the case of confirming the measurement result 51, it is possible to confirm the measurement result 51 which has the first identification information 31 associated with the second identification information 41 without manual input by using the second identification information 41. As a result, it is possible to easily suppress the erroneous input and associate the measurement result 51 with the subject information without using an integrated management system.

Method for Manufacturing Reagent Kit

Next, a method of manufacturing a reagent kit will be described. The method of manufacturing the reagent kit of the present embodiment is a method of manufacturing the reagent kit 100 used for measuring a sample by the sample measuring apparatus 300. A method for producing a reagent kit includes the following steps. (1) House a container 10 having a housing part 11 for containing a reagent that reacts with a sample in an unsealable container 20. (2) Attach the first identification label 30 including the first identification information 31 read by the sample measuring apparatus 300 and associated with the measurement result 51 of the sample to the reagent kit 100. (3) Attach the second identification label 40, which includes the second identification information 41 associated with the first identification information 31 and is provided so as to be attachable to the recorded item of the subject information, to the reagent kit 100.

The order of execution of steps (1), (2), and (3) is not necessarily limited to numerical order. When attaching at least one of the first identification label 30 and the second identification label 40 to the container 10 in steps (2) and (3), the step may be performed prior to step (1). In the case of attaching at least one of the first identification label 30 and the second identification label 40 to the housing body 20 in steps (2) and (3), the step may be either before or after the step (1).

In the method of manufacturing a container described above, when the sample measurement using the container 10 is performed, the first identification information 31 read from the first identification label 30 is associated with the measurement result 51 by attaching the first identification label 30 to the reagent kit 100. When performing a sample measurement using the container 10, the user affixes the second identification label 40 to the recorded item of the subject information such as a chart 90 or the like of the subject from whom the sample was collected by attaching the second identification label 40 to the reagent kit 100. As a result, the subject information and the information of the measurement result 51 of the subject can be associated with each other based on the second identification information 41 and the first identification information 31. In addition, it is not necessary for the user to manually input the subject information to the sample measuring apparatus every time the user performs a sample measurement, and the first identification information 31 given to the measurement result 51 and the second identification information 41 can be reliably associated. As a result, it is possible to suppress erroneous input and easily associate the measurement result with the subject information without using an integrated management system.

Next, a configuration example of each part of the reagent kit 100 will be described.

Housing Body

Figure 2A:
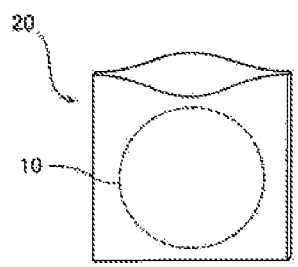
FIGS. 2A and 2B are schematic views showing configuration examples of a housing body.

In the example of FIG. 2A, the housing body 20 is a bag. The housing body 20 is a bag made of a functional film having gas-proof and moisture-proof properties. The housing body 20 is, for example, an aluminum laminate bag made of an aluminum laminate film. In this way it is possible to obtain the housing body 20 capable of suppressing the deterioration of the container 10 even during storage, while reducing the packaging size as compared with a packaging box or the like. Gas-proofness and moisture-proofness mean properties that make outside gas and water vapor difficult to permeate.

Figure 2B:
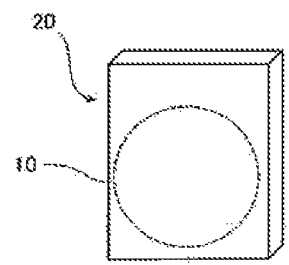

In the example of FIG. 2B, the housing body 20 is a box body. In order to ensure gas-proofness and moisture-proofness of the container 10, the container 10 may be wrapped with a functional film and then stored in the housing body 20.

Identification Label

The first identification label 30 and the second identification label 40 include, for example, a machine-readable information recording medium.

Figure 3A:
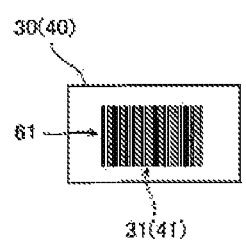
FIGS. 3A, 3B and 3C are schematic diagrams showing a bar code (3A), a multidimensional code (3B), and an RF tag (3C) in which identification information is recorded.

In the example of FIG. 3A, the first identification label 30 and the second identification label 40 include a bar code 61. The first identification information 31 and the second identification information 41 are recorded in the bar code 61, respectively.

Figure 3B:
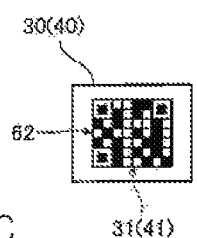

In the example of FIG. 3B, the first identification label 30 and the second identification label 40 include a multidimensional code 62. In FIG. 3B, the multidimensional code 62 is a two-dimensional code. The first identification information 31 and the second identification information 41 are respectively recorded in the multidimensional code 62.

According to the examples of FIGS. 3A and 3B, the first identification information 31 and the second identification information 41 can be easily read in a contactless manner by optical reading using an optical scanner or a camera such as a barcode reader.

Figure 3C:
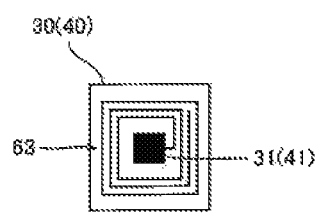

In the example of FIG. 3C, the first identification label 30 and the second identification label 40 include an RF tag 63. The RF tag 63 has an IC that can read and write information, and an antenna. The first identification information 31 and the second identification information 41 are respectively recorded in the RF tag 63.

According to the example of FIG. 3C, the first identification information 31 and the second identification information 41 can be easily read in a contactless manner by short-range wireless communication of an RF tag reader.

The first identification label 30 and the second identification label 40 may include the same type of information recording medium such that both the first identification label 30 and the second identification label 40 are multidimensional codes, and may include different kinds of information recording media such as tags and bar codes. The second identification label 40 also may be an information recording medium which is not machine-readable.

Attachment Form of Identification Label

The first identification label 30 and the second identification label 40 may be attached to either the container 10 or the housing body 20.

Figure 4:
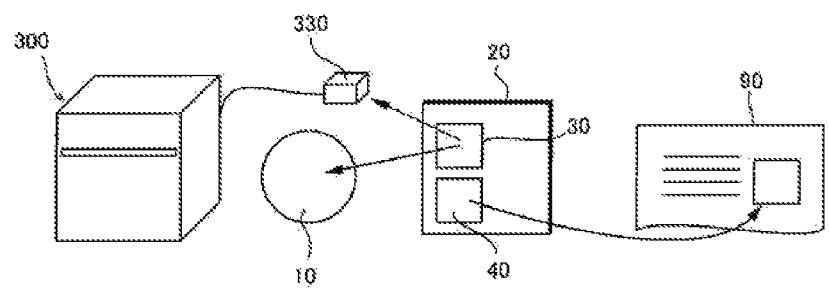
FIG. 4 is a schematic view showing an example in which first and second identification labels are attached to a housing body.

In the example of FIG. 4, both the first identification label 30 and the second identification label 40 are attached to the housing body 20. Specifically, the first identification label 30 and the second identification label 40 are affixed to the outer surface of the housing body 20 in a releasable state. After the housing body 20 is opened and the container 10 is taken out, the first identification label 30 is peeled from the housing body 20 and attached to the container 10. When the container 10 is set in the apparatus, the sample measuring apparatus 300 automatically reads the first identification information 31 of the first identification label 30. The reading of the first identification information 31 also may be performed by a reading unit 330 included in the sample measuring apparatus 300 while the first identification label 30 remains attached to the housing body 20. The second identification label 40 is peeled from the housing 20 and attached to the chart 90.

By attaching the first identification label 30 and the second identification label 40 to the housing body 20 in this manner, the user can easily recognize the presence of the first identification label 30 and the second identification label 40. The second identification label 40 can be easily separated and attached to the medical record 90 or the like in contrast to when the second identification label 40 is attached to the container 10.

Figure 5:
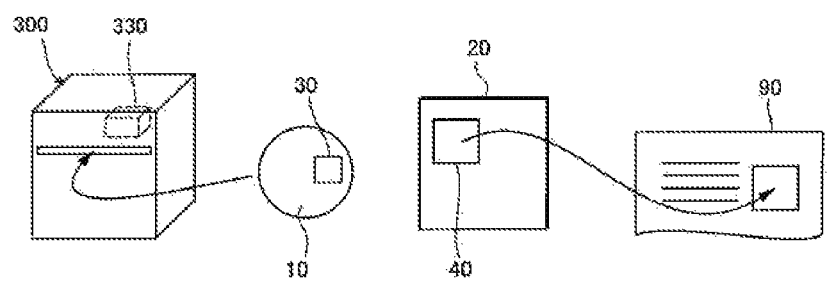
FIG. 5 is a schematic view showing an example in which a first identification label is attached to a container and a second identification label is attached to a housing body.

In the example of FIG. 5, the first identification label 30 is attached to the container 10, and the second identification label 40 is attached to the housing body 20. Specifically, the first identification label 30 is affixed to the outer surface of the container 10 in a state which cannot be detached. When the container 10 is set in the apparatus, the sample measuring apparatus 300 automatically reads the first identification information 31 of the first identification label 30. The second identification label 40 is affixed to the outer surface of the housing body 20 in a releasable state. The second identification label 40 is peeled from the housing 20 and attached to the chart 90.

When setting the container 10 in the sample measuring apparatus 300, the first identification information 31 is read from the first identification label 30 provided in the container 10 by providing the first identification label 30 on the container 10 as described above. As a result, it is possible to omit the work of the user attaching the first identification label 30 to the container 10. Since the second identification label 40 is attached to the container 20, the second identification label 40 can be easily separated and attached to the chart 90 or the like, as compared with when the second identification label 40 is attached to the container 10.

Figure 6:
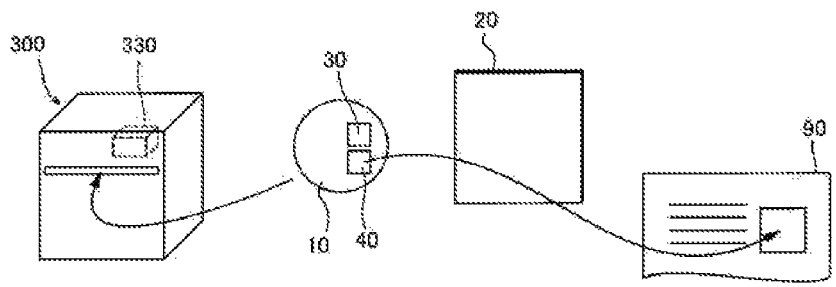
FIG. 6 is a schematic view showing an example in which first and second identification labels are attached to a container.

In the example of FIG. 6, both the first identification label 30 and the second identification label 40 are attached to the container 10. Specifically, the first identification label 30 is affixed to the outer surface of the container 10 in a state which cannot be detached. When the container 10 is set in the apparatus, the sample measuring apparatus 300 automatically reads the first identification information 31 of the first identification label 30. The second identification label 40 is affixed to the outer surface of the container 10 in a peelable and detachable state. After the housing body 20 is unsealed and the container 10 is taken out, the second identification label 40 is peeled from the container 10 and affixed to the chart 90.

When both the first identification label 30 and the second identification label 40 are attached to the container 10 as shown in FIG. 6 and the container 10 is used, the user can reliably recognize the presence of the first identification label 30 and the second identification label 40. Regarding the first identification label 30, it also is possible to omit an operation for the user to paste the first identification label 30 on the container 10.

As shown in FIGS. 4 to 6, it is preferable that the first identification label 30 is provided in the container 10. In this way when setting the container 10 in the sample measuring apparatus 300, it is possible to read the first identification information 31 directly from the first identification label 30 provided on the container 10. As a result, it is possible to omit the work of the user attaching the first identification label 30 to the container 10. The first identification label 30 may be separably provided in the housing body 20, or may be housed in the housing body 20 together with the container 10.

As shown in FIGS. 4 to 6, the second identification label 40 also may be separably provided in either the container 10 or the housing body 20. The second identification label 40 may be accommodated in the housing body 20 together with the container 10. In this way the user can easily remove the second identification label 40 from the reagent kit 100 and attach it to the medical record 90 or the like.

As shown in FIGS. 4 to 6, the second identification label 40 is a label provided so as to be affixed to an object. In this way it possible to easily attach the second identification label 40 on the recorded matter of the subject information such as the chart 90, for example, unlike the type of label that cannot be adhered.

In the examples of FIG. 7, the second identification label 40 is provided so as to overlap the first identification label 30 in a state in which it can be separated from the first identification label 30. The second identification label 40 overlaps a part of the first identification label 30 so that both the second identification label 40 and the first identification label 30 can be visually recognized.

Figure 7A:
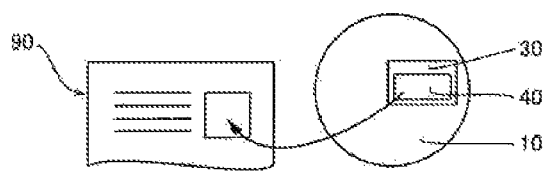
FIGS. 7A and 7B are diagrams showing examples in which the first and second identification labels overlap.

In FIG. 7A, the first identification label 30 is provided on the outer surface of the container 10 with the second identification label 40 superimposed on the first identification label 30. After the housing body 20 is opened and the container 10 is taken out, the second identification label 40 is peeled off the first identification label 30 and affixed to the chart 90.

Figure 7B:
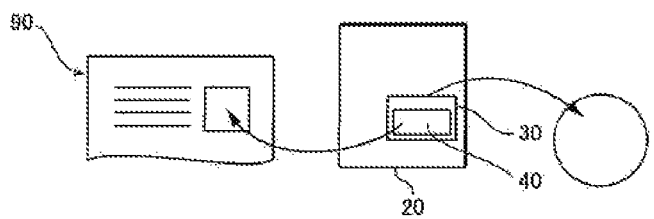

In FIG. 7B, the first identification label 30 is provided on the outer surface of the housing body 20 in a state in which the second identification label 40 is pasted on the first identification label 30. The second identification label 40 is separated from the top of the first identification label 30 and affixed to the chart 90. After the housing body 20 is opened and the container 10 is taken out, the first identification label 30 is peeled from the housing 20 and attached to the container 10.

In the example of FIGS. 7A and 7B, since the second identification label 40 overlaps the first identification label 30, the user can recognize that the second identification label 40 must be peeled off and pasted on the recorded item of the subject information such as the chart 90.

Figure 8:
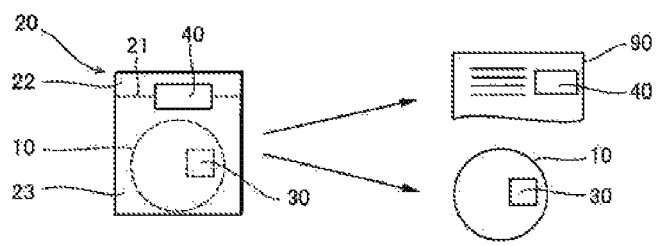
FIG. 8 is a view showing an example in which a second identification label is provided at an unsealing position of a housing body.

In the example of FIG. 8, the unseal position 21 is defined in the housing body 20, and the second identification label 40 is provided on the housing body 20 so as to overlap with the unseal position. The unseal position 21 is configured as a boundary line between, for example, the separating part 22 separated at the time of opening and the housing part 23 where the container 10 is disposed. When the user grips and pulls the separating part 22, the housing body 20 is opened with the unseal position 21 as a boundary. The second identification label 40 is affixed to the unseal position 21 so as to straddle the separating part 22 and the housing part 23. At the time of opening, the housing body 20 can be unsealed by separating the second identification label 40 from the housing body 20. When opening the housing body 20, the user separates the second identification label 40 from the housing body 20 and adheres it to the chart 90 or the like.

In the example of FIG. 8, when the user unseals the housing body 20, the second identification label 40 can be reliably separated and attached to the chart 90 or the like.
Identification Information The contents of the first identification information 31 and the second identification information 41 are not particularly limited insofar as they are information that uniquely associates with each other. Information other than the first identification information 31 and the second identification information 41 also may be recorded in the first identification label 30 and the second identification label 40, respectively.

Figure 9:
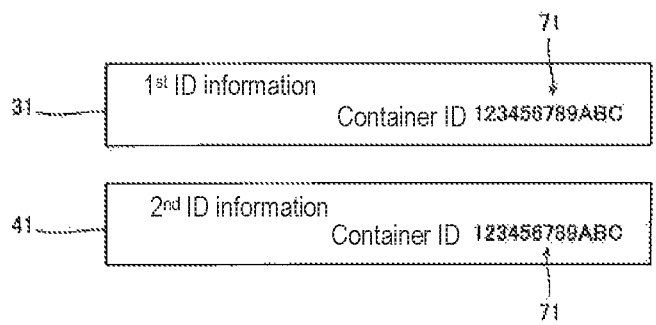
FIG. 9 is a diagram showing specific examples of first and second identification information.

In the example of FIG. 9, the first identification information 31 includes information 71 for identifying the container 10. The information 71 for identifying the container 10 is unique information that can uniquely identify the container 10, such as the container ID and serial number of the container 10, for example. In the example of FIG. 9, the second identification information 41 also includes the same container ID as the first identification information 31. The second identification information 41 and the first identification information 31 are uniquely associated by the common container ID.

In this way not only is the measurement result 51 to the subject information associated by the first identification information 31, the container 10 used for generating the measurement result 51 also is identified by the information 71 for identifying the container 10. It is possible to avoid, for example, specifying the use of a container other than a genuine product or reuse of a used container, as well as inappropriate measurement by reading the information 71 for identifying the container 10 at the start of the measurement by the sample measuring device 300. In addition, traceability of each container 10 can be ensured for quality control.

Figure 10:
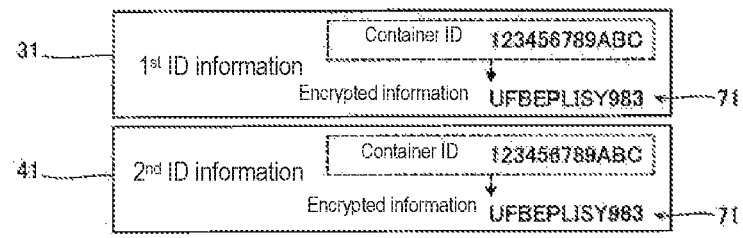
FIG. 10 is a diagram showing an example in which the first and second identification information include encrypted information.
Figure 10:
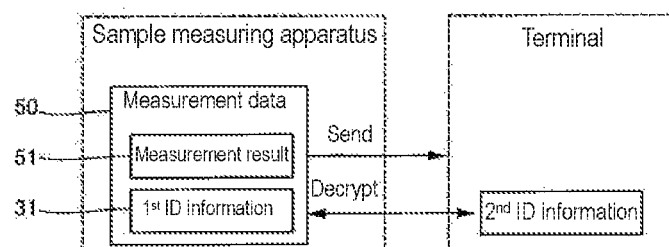
Figure 11:
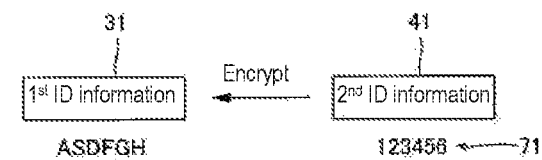
FIG. 11 is a diagram showing an example in which the first and second identification information are corresponding information.
Figure 11:
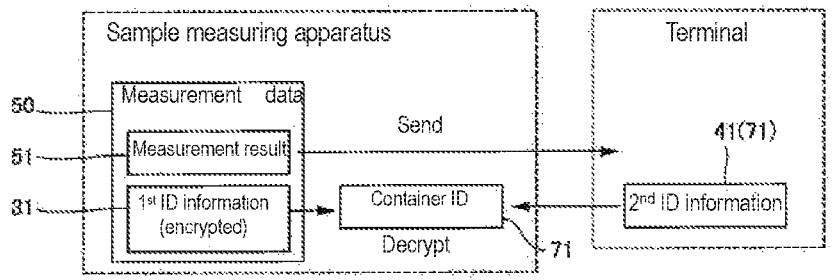

Here, as shown in FIG. 10 and FIG. 11, the second identification information 41 includes the same or corresponding information as the first identification information 31. Here, the corresponding information is information different from the first identification information 31 but which has a one-to-one correspondence to the first identification information 31. In this way the second identification information 41 and the first identification information 31 can be associated easily and reliably.

In FIG. 10, the second identification information 41 includes the same encrypted information as the first identification information 31. Specifically, both the first identification information 31 and the second identification information 41 include the same encryption information in which the container ID of the container 10 is encrypted. Upon reading the first identification information 31, the sample measuring apparatus 300 decrypts the information and returns it to the container ID, then generates the measurement result data 50 and associates the result data with the measurement result 51. When browsing the measurement result 51, the user operates the terminal 500 managing the subject information, reads the second identification information 41 from the second identification label 40, decrypts the information, returns the information to the container ID, and references the measurement result data 50 by the terminal 500. In this way the measurement result data 50 including the same container ID is acquired by the terminal 500. A unique decryption key provided only to the user of the sample measuring apparatus 300 and the terminal 500 is used for decoding the first identification information 31 and the second identification information 41. Even if the first identification information 31 is acquired by a third party who does not have a unique decryption key, the decrypted container ID is never acquired, so a third party cannot acquire the measurement result 51.

In the example of FIG. 10, reading by a third party other than the user can be prevented since the first identification information 31 and the second identification information 41 are encrypted. Only the user can manage the subject information and the measurement result 51 in association with each other by making it possible to decrypt using the decryption key which is information managed by the user.

In the example of FIG. 11, the first identification information 31 includes information obtained by converting the second identification information 41 by a predetermined method. Conversion by a predetermined method is to change the second identification information 41 to another information by a predetermined method, and includes the calculation of a hash value by a predetermined hash function in addition to encryption. In the example of FIG. 11, the second identification information 41 includes the container ID of the container 10 as the pre-conversion information. The first identification information 31 includes information obtained by encrypting the container ID by a predetermined method as the converted information.

When browsing the measurement result 51, the user operates the terminal 500 managing the subject information to read the second identification information 41 from the second identification label 40. In the sample measuring apparatus 300 in which the decoding method is set in advance, the container ID which is the decoded first identification information 31 and the container ID which is the second identification information 41 are checked to specify the measurement result data 50.

In this way, the first identification information 31 and corresponding second information 41 associated with the measurement result 51 can be checked by reverse conversion of the first identification information 31 by a predetermined method and returning it to the second identification information 41. A third party who does not know the conversion method cannot check the first identification information 31 with the corresponding second identification information 41. When the first identification information 31 is a hash value, the terminal 500 calculates a hash value of the container ID of the second identification information 41, and checks the value with the hash value of the first identification information 31 included in the measurement result data 50. In this way the first identification information 31 associated with the measurement result 51 and the corresponding second identification information 41 can be checked by reverse conversion of the second identification information 41 by a predetermined method and checking with the first identification information 31.

Figure 12:
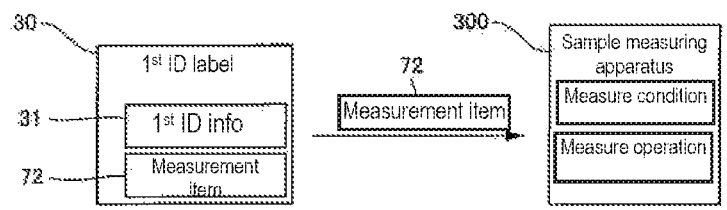
FIG. 12 is a diagram showing a first example in which a first identification label includes information relating to measurement.
Figure 13:
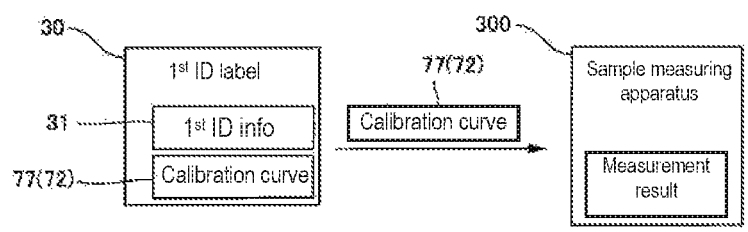
FIG. 13 is a diagram showing a second example in which the first identification label includes information relating to measurement.
Figure 14:
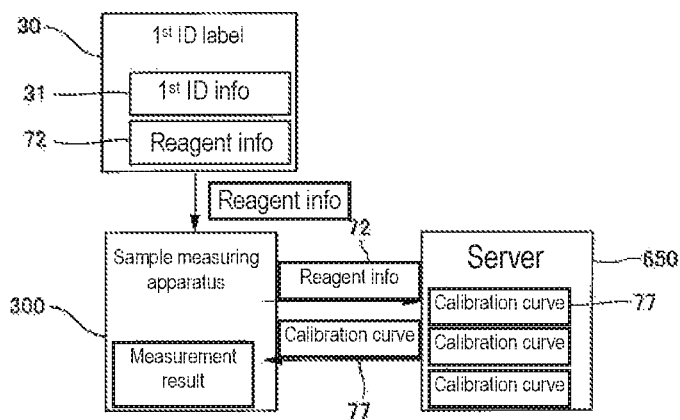
FIG. 14 is a diagram showing a third example in which the first identification label includes information relating to measurement.

In the example shown in FIGS. 12 to 14, the first identification label 30 includes information 72 relating to measurement using the container 10. The sample measuring apparatus 300 executes a measuring operation according to the measurement related information 72 read from the first identification label 30. In this way information necessary for measurement can be acquired from the first identification label 30. For example, the type of the container 10 is specified based on the measurement-related information 72, and the measurement operation corresponding to the specified container 10 is executed in the sample measurement apparatus 300. In this way the type of the container 10 is understood through the information 72 relating to the measurement using the container 10, and the sample measuring apparatus 300 can perform the measuring operation according to the type of the container 10.

In FIG. 12, information 72 relating to measurement using the container 10 includes information related to measurement items. The sample measuring apparatus 300 reads the information of the measurement items from the first identification label 30, selects the measurement condition and measurement operation pattern previously set for each measurement item, and executes the measurement using the container 10.

In FIG. 12, the information 72 relating to measurement using the container 10 may include information on measurement conditions. The sample measuring apparatus 300 reads the measurement condition information from the first identification label 30 and executes the measurement using the container 10 according to the read measurement condition. In this case, it is unnecessary to previously set measurement conditions for each measurement item in the sample measurement apparatus 300. The information 72 relating to measurement using the container 10 may include both measurement items and measurement conditions. In this way even if the user does not separately input the information of the measurement item or the measurement condition by manual input, a suitable measurement operation can be performed by the sample measuring apparatus 300 by recording the measurement condition and the information of the measurement item as the measurement-related information 72.

In FIG. 13, the information 72 relating to the measurement using the container 10 includes the information on the calibration curve 77. The calibration curve 77 is information associating the measurement result of the test substance using the container 10 with the amount of the test substance, and is set for each reagent contained in the container 10. The calibration curve 77 is prepared, for example, for each production lot number. Therefore, when the lot number of the contained reagent is different, separate calibration curves 77 are used even in the same container 10. Therefore, by including information on the calibration curve 77 corresponding to the reagent contained in the container 10 as the measurement-related information 72, the sample measuring apparatus 300 uses the calibration curve 77 read from the first identification label 30 directly to generate the measurement result 51. In this way a measurement can be accurately performed without separately preparing a calibration curve by a user operation.

As another example of the method of obtaining the calibration curve 77, in the example of FIG. 14 the information 72 relating to the measurement using the container 10 includes information on the reagent contained in the container 10. The information of the reagent contained in the container 10 is, for example, the lot number of the above-mentioned reagent. The sample measuring apparatus 300 transmits the lot number read from the first identification label 30 to the server 650 that manages the reagent information, and requests the information of the calibration curve 77 corresponding to the lot number. The server 650 managing the reagent information stores a calibration curve 77 prepared for each lot number is recorded by the manufacturer of the container 10 or the manufacturer of the reagent stored in the container 10. The sample measuring apparatus 300 acquires the calibration curve 77 corresponding to the lot number as a response from the server 650 managing the reagent information.

Figure 15A:
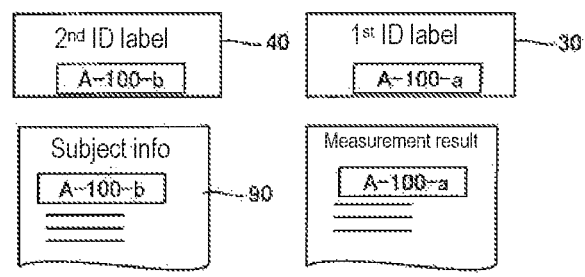
FIGS. 15A and 15B are diagrams showing an example (15A) in which the first and second identification labels include common text and an example (15B) including a common graphic.
Figure 15B:
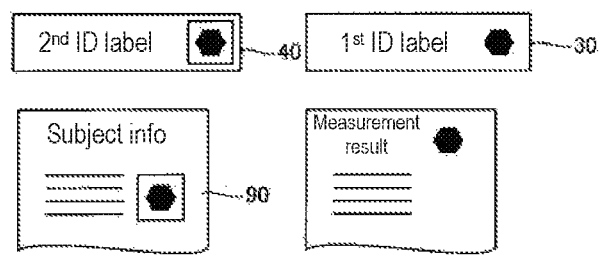

As shown in FIGS. 15A and 15B, the first identification information 31 and the second identification information 41 may include the same text or graphic. In the example of FIG. 15A, the first identification information 31 and the second identification information 41 have the same text. Specifically, the first identification information 31 of the first identification label 30 includes the character "A-100-a", and the second identification information 41 of the second identification label 40 contains the character "A-100-*b*". In the second identification label 40, characters that are the second identification information 41 are displayed so as to be visually recognizable. In this way, before the machine-reading is performed, the first identification information :31 visually associated by the user and the second identification Information 41 are associated and managed by the part "A-100" that is common to the first identification information 31 and the second identification information 41. The same text is, for example, the container ID of the container 10.

In the example of FIG. 15B, the first identification information 31 and the second identification information 41 have the same graphic. Specifically, the first identification information 31 of the first identification label 30 and the second identification information 41 of the second identification label 40 commonly include hexagonal figures. In the second identification label 40, characters that are the second identification information 41 are displayed so as to be visually recognizable. In this way the user can visually manage the first identification information 31 and the second identification information 41 in association with each other by using a graphic common to the first identification information 31 and the second identification information 41.

In addition, the measurement result 51 is associated with text and graphic included in the first identification information 31. Even when printing the measurement result 51 or the like, it is possible to recognize the correspondence relationship at a glance by common text and graphics. In this way, in the example of FIGS. 15A and 15B, since the correspondence relationship between the first identification information 31 and the second identification information 41 can be visually recognized, for example, when the user uses a plurality of the reagent kits 100, the user can visually distinguish the second identification information 41 of each reagent kit 100 even in a case where a sample measurement is to be performed for a plurality of subjects.

Figure 16A:
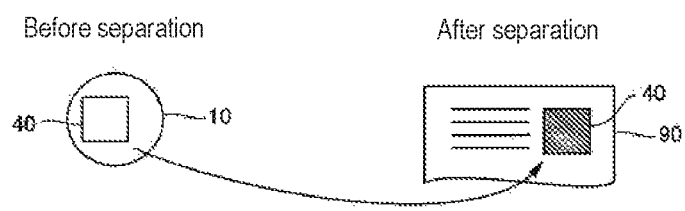
FIGS. 16A and 16B are diagrams showing a first example (16A) and a second example (16B) of a second identification label the appearance of which changes before and after separation.
Figure 16B:

In the example of FIGS. 16A and 16B, the second identification label 40 is separably provided in either the container 10 or the container 20, and is configured so that its appearance changes before and after separation. Specifically, in FIG. 16A, the second identification label 40 is provided in the container 10, and shows an example where the color changes when separated by the user. In FIG. 16A, the color before change is shown in solid color and the color after change is indicated by hatching. In FIG. 16B, the second identification label 40 is provided in the housing body 20, and shows an example where the pattern changes when separated by the user. In FIG. 16B, a border pattern indicated by hatching is generated in the peripheral portion of the second identification label 40 after separation as contrasted with the solid color before separation.

In the configuration example of FIGS. 16A and 16B, it is possible for the user to grasp at a glance that the second identification label 40 has been used, due to the appearance change. Therefore, even when a plurality of reagent kits 100 are used, it is possible for the user to visually distinguish the second identification information 41 of each reagent kit 100.

Figure 17A:
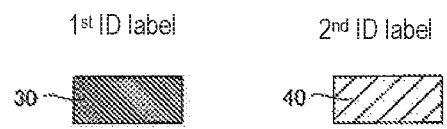
FIGS. 17A, 17B and 17C are views showing an example in which the color (17A), shape (17B), and pattern (17C) of the first and second identification labels differ.
Figure 17B:
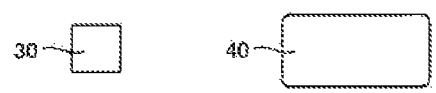
Figure 17C:

In the example of FIGS. 17A, 17B and 17C, the first identification label 30 and the second identification label 40 have different shapes, colors or patterns so as to be visually distinguishable. In this way the user can easily distinguish between the first identification label 30 and the second identification label 40. Therefore, it is possible to enable the user to more reliably recognize which label should be attached to the chart 90.

In FIG. 17A, colors are different between the first identification label 30 and the second identification label 40. In FIG. 17A, color differences are indicated by hatching type differences. In FIG. 17B, the first identification label 30 and the second identification label 40 have different shapes. The first identification label 30 has a square shape, and the second identification label 40 has a rectangular shape with rounded corners. In addition, the first identification label 30 is smaller in size than the second identification label 40. In this way the first identification label 30 and the second identification label 40 may have different sizes. In FIG. 17C, the first identification label 30 and the second identification label 40 have different patterns. In FIG. 17C, the first identification label 30 is a solid color and the second identification label 40 is given a star-shaped pattern at the corner portion. The shapes, colors or patterns of the first identification label 30 and the second identification label 40 are arbitrary, and any shape, color, pattern may be used insofar as they can be visually distinguished from each other. The identification labels also may be visually distinguishable by plural combinations of shape, color and pattern.

Specific Configuration Example of Reagent Kit

Figure 18:
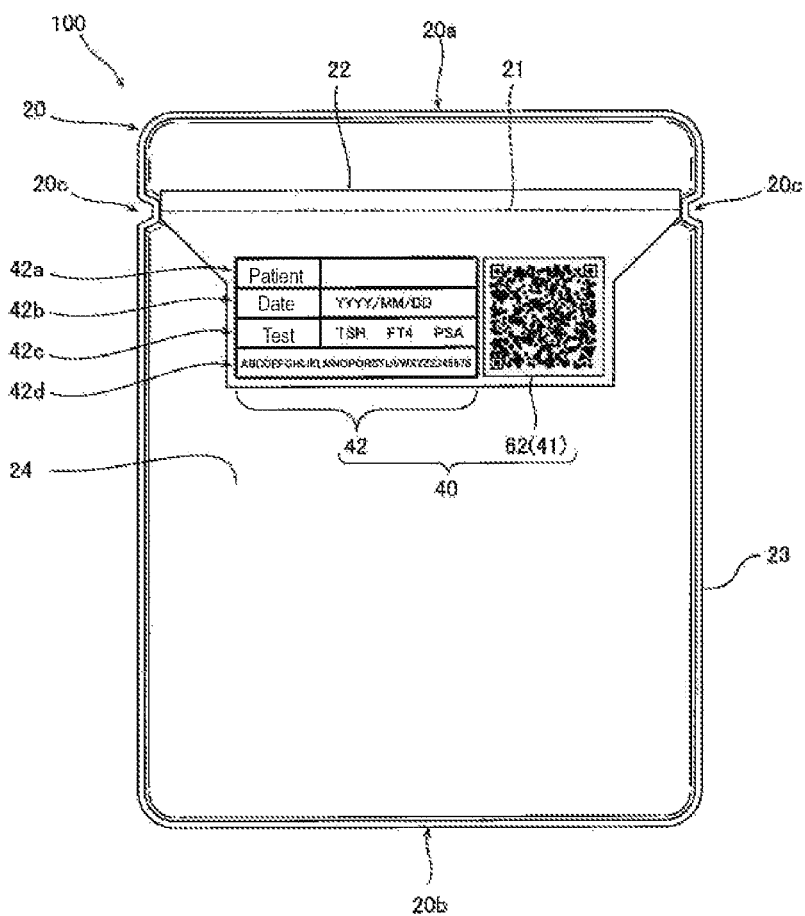
FIG. 18 is a diagram on the front side in a specific configuration example of the reagent kit.
Figure 19:
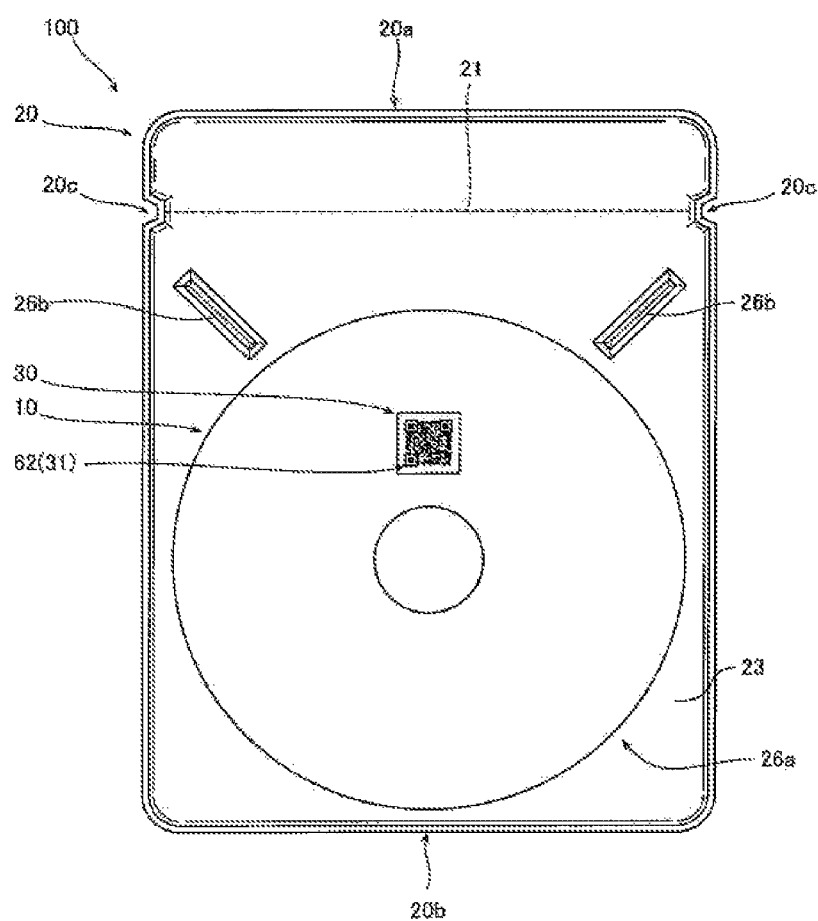
FIG. 19 is an internal view of a specific configuration example of a reagent kit.
Figure 20:
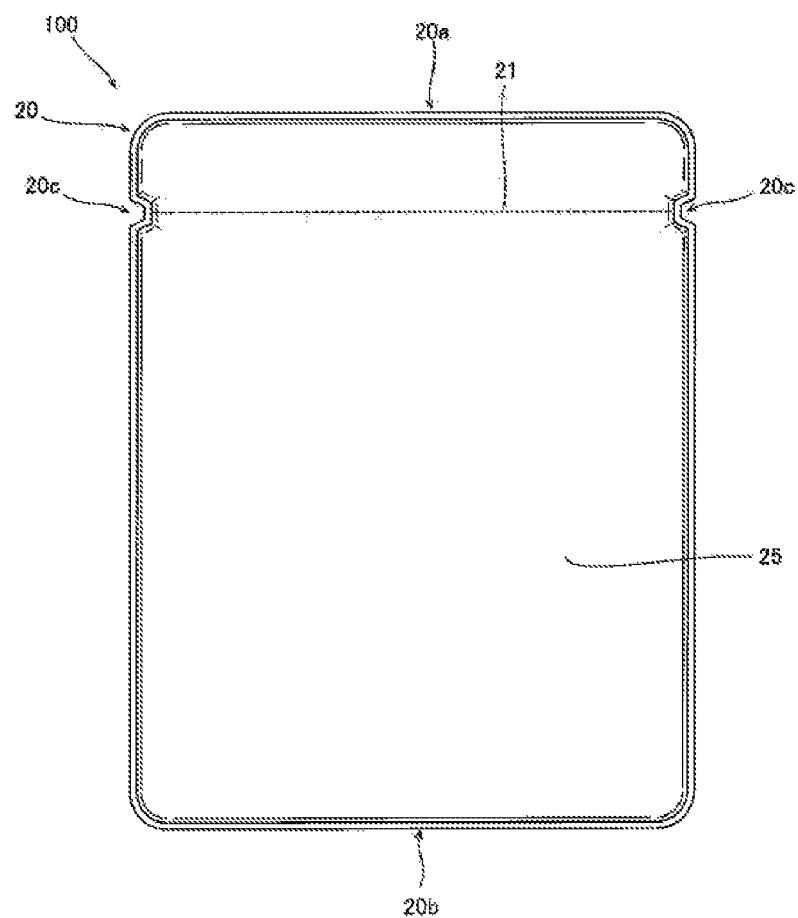
FIG. 20 is a diagram of a back side in a concrete configuration example of a reagent kit.

FIG. 18 to FIG. 20 show a specific configuration example of the reagent kit 100 described above. FIG. 18 shows the surface of the housing body 20, FIG. 19 shows the internal structure of the housing body 20, and. FIG. 20 shows the rear surface of the housing body 20.

As shown in FIGS. 18 and 20, the housing body 20 has a structure in which a sheet-like surface member 24 and a back surface member 25 are bonded together at the outer peripheral edge portion. The surface member 24 and the back surface member 25 are made of an aluminum laminate material or the like and have gas-proof and moisture-proof properties. The housing body 20 has a rectangular shape in which the vertical direction is the long side direction in the drawing, and has a notch 20c for unsealing in the vicinity of one end 20a of the pair of long sides (in the vicinity of the upper end in FIG. 18). When the user pulls the space between the pair of notches 20c in the short side direction, the one end portion 20a side is separated from the housing body 20.

A separating part 22 is provided in the housing body 20 so as to connect between the pair of notches 20c. The separating part 22 is made of a material which is harder to cut than the other housing part 23 of the housing body 20, and is provided on the surface of the housing body 20. Therefore, when the one end 20a side is separated from the housing body 20, the housing body 20 is cut along the boundary line in the short side direction connecting the pair of notches 20c, the separating part 22 is separated from the container 20 while maintaining its shape without cutting. In the example of FIG. 18, a pair of notches 20c and a boundary line connecting between the pair of notches 20c are defined as unseal position 21.

As shown in FIG. 19, inside the housing body 20 are provided an arrangement area 26a in which a disk-shaped container 10 is arranged and a projection part 26b for preventing displacement of the container 10. The projection part 26b is disposed between the pair of notches 20c and the arrangement area 26a, and the arrangement area 26a is regulated on the side of the other end 20b of the housing body 20. The projection part 26b protrudes in the thickness direction of the housing body 20 and makes contact with the end face of the container 10 so that the container 10 disposed in the arrangement area 26a does not move to the one end part 20a side due to vibration or the like during transport. In this way the container 10 is prevented from being caught between the notches 20c when the housing body 20 is unsealed.

In the examples of FIGS. 18 to 20, the second identification label 40 is provided on the housing body 20 so as to overlap the unseal position 21, and the second identification label 40 is separated from the housing body 20 in conjunction with the unsealing of the housing body 20. That is, the second identification label 40 is affixed to the separating part 22 on the outer surface of the housing body 20. Therefore, when the one end 20a side is separated from the housing body 20, the second identification label 40 is separated from the housing body 20 together with the separating part 22. Since the separating part 22 cannot be cut and is separated from the housing body 20 while maintaining its shape, it is possible to avoid erroneously cutting out the second identification label 40 during unsealing. When the housing body 20 is opened, the second identification label 40 is separated from the housing body 20, so that when the user unseals the housing body 20, the second identification label 40 can be reliably separated and affixed to the medical record 90 and the like.

In the example of FIG. 18, the second identification label 40 also has an entry area 42 for entering information. The second identification label 40 includes the multidimensional code 62 in which the second identification information 41 is recorded, and the entry area 42. By providing the entry area 42, when measuring using the container 10, the user directly fills in the second identification label 40 with the measurement date and time of measurement, measurement items and the like, and then inserts the second identification label 40 onto the chart 90 or the like. Therefore, the management of the subject information and the measurement result 51 can be facilitated.

In the example of FIG. 18, the entry area 42 includes a patient information entry column 42a, an examination date entry column 42b, an examination item entry column 42c, and an information display column 42d. The name or subject ID of the subject from whom the sample was collected is entered in the patient information entry column 42a. The date on which the sample measurement was performed using the container 10 is entered in the examination date entry column 42b. Measurement items of the container 10 are entered in a selection form from a plurality of options in the inspection item entry column 42c. For example, the container ID of the container 10 is described in the information display column 42d. The container ID is the same information as the second identification information 41 recorded in the multidimensional code 62. In this way the container ID can be directly input even if the user cannot read the multidimensional code 62 for some reason.

In the example of FIG. 19, the first identification label 30 is attached to the container 10. The first identification label 30 includes the multidimensional code 62 in which the first identification information 31 is recorded. In the first identification label 30, the entry area 42 is not provided, and it is a small label. When the container 10 is set in the sample measuring apparatus 300 by the user, the first identification information 31 is automatically read from the multidimensional code 62 of the first identification label 30.

Third Identification Label

The reagent kit 100 may include a third identification label in addition to the first identification label 30 and the second identification label 40. Note that the reagent kit 100 also may include a fourth identification label, a fifth identification label, and the like.

Figure 21:
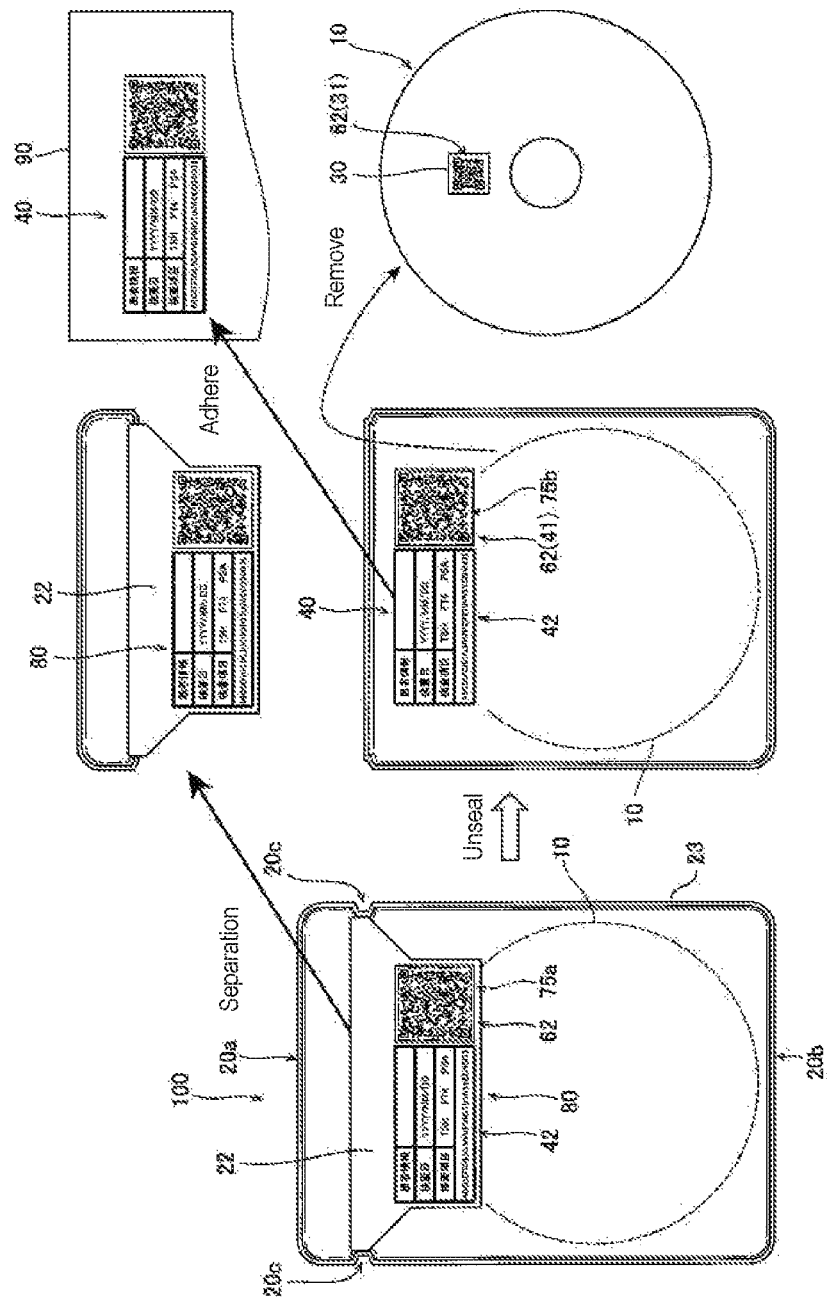
FIG. 21 is a diagram showing a configuration example in which a third identification label is provided in a reagent kit.

In the example of FIG. 21, the reagent kit 100 further includes a third identification label 80 provided in the housing body 20. The third identification label 80 is provided so as to be separated from the housing body 20 by unsealing the housing body 20, and the second identification label 40 is provided so that it can be separated from the housing body 20 by unsealing the housing body 20. In this way the information of the third identification label 80 can be used when the container 20 is unused before being opened, and the information of the second identification label 40 can be made available after opening.

Specifically, in FIG. 21, the unseal position of the housing body 20 is regulated, the third identification label 80 is attached so as to overlap the unseal position 21, and the second identification label 40 is attached to the housing body 20 so that the second identification label 40 is exposed from the housing body 20.

That is, in place of the second identification label 40 of FIG. 18, a third identification label 80 is provided in the separating part 22. In FIG. 21, the second identification label 40 is arranged so as to overlap the lower side of the separating part 22. That is, the second identification label 40 is directly affixed to the outer surface of the housing body 20, and the separating part 22 to which the third identification label 80 is affixed is attached so as to overlap the second identification label 40. The separating part 22 is affixed to the outer surface of the housing body 20 in a region other than the region overlapping with the second identifying label 40.

It is possible to expose the second identification label 40 while separating the third identification label 80 by unsealing the housing body 20, such that it is possible to avoid confusion between the third identification label 80 and the second identification label 40.

When the user unseals the housing body 20, the housing body 20 is cut off along the boundary line from the notches 20c, and the separating part 22 is separated from the housing portion 23 of the housing body 20. In this way the third identification label 80 is separated from the housing body 20 together with the separating part 22, and the second identification label 40 is exposed to the outside in the remaining housing portion 23. The user peels off the second identification label 40 and adheres it on the chart 90. The user can remove the container 10 to which the first identification label 30 has been attached from the housing portion 23 and set the container 10 in the sample measuring device 300.

The third identification label 80 and the second identification label 40 have substantially the same shape and each include a multidimensional code 62 and an entry area 42. The third identification label 80 and the second identification label 40 are arranged so as to overlap each other so that the positions of the entry areas 42 are coincident. The second identification label 40 is configured so that the contents entered in the entry area 42 of the third identification label 80 by the user are directly transferred to the entry area 42 of the second identification label 40. In this way it is possible to eliminate the trouble of writing the same information on the second identification label 40 again when collecting samples after unsealing or performing sample measurement with the container 10 by the user performing preparatory work enters the subject information or the like on the third identification label 80 before unsealing.

Common identification information can be recorded in the third identification label 80 and the second identification label 40. Different information also can be recorded in the third identification label 80 and the second identification label 40.

Specifically, the third identification label 80 includes information 75a indicating that it is before unsealing, and the second identification label 40 includes information 75b indicating that it has been unsealed. For example, the container ID of the container 10 is recorded as common identification information in the third identification label 80 and the second identification label 40, and information for distinguishing whether it is before unsealing or unsealed can be entered as different information. If the information on the third identification label 80 is read before unsealing, the machine ID can be read as well as the container ID before it is unsealed. Information cannot be read before opening, since the second identification label 40 is not exposed. When the housing body 20 is unsealed, information can be read from the second identification label 40 for the first time, and it can be machine read that the container ID has been opened together with the container ID. In this way it is possible to reliably identify whether the reagent kit 100 is unsealed before opening or after opening by the third identification label 80 and the second identification label 40. Therefore, it is possible to avoid reusing a used container 10 by mistake. It is also useful for stock management of the reagent kit 100.

Figure 22:
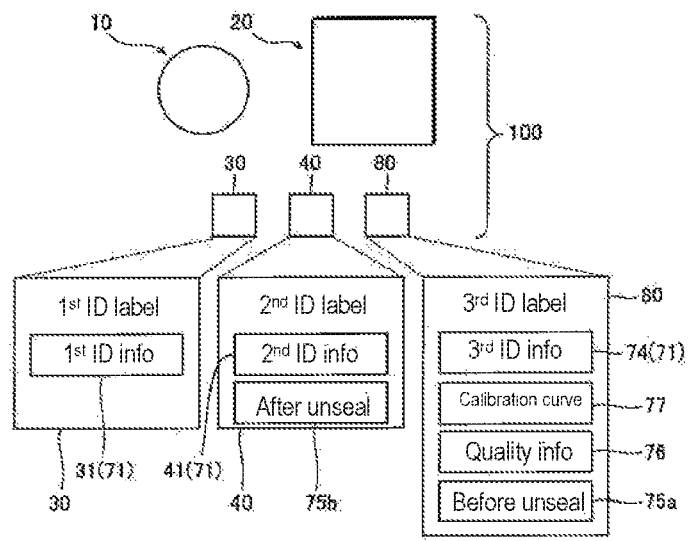
FIG. 22 is a view showing information recorded in first to third identification labels.

FIG. 22 shows an example of information recorded on the third identification label 80. In FIG. 22, the third identification label 80 includes at least one of information 71 for identifying the container 10, information 76 on the quality of the container 10, and a calibration curve 77.

The information 71 for identifying the container 10 is, for example, the container ID of the container 10. In other words, the third identification label 80 includes the third identification information 74; and the first identification information 31, the second identification information 41, and the third identification information 74 include the information 71 for identifying the common container 10. In this way the third identification label 80 can be used for stock management or the like.

Figure 23A:
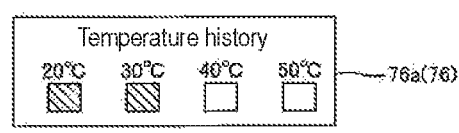
FIGS. 23A and 23B are diagrams showing examples of information recorded on a third identification label.
Figure 23B:
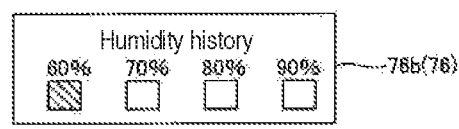

The information 76 on the quality of the container 10 includes, for example, information on the temperature history and the humidity history of the reagent kit 100. Specifically, the third identification label 80 includes at least either the information of the temperature-indicating label region 76a (see FIG. 23A) and the humidity-indicating label region 76b (see FIG. 23B) as the information 76 on the quality of the container 10.

The temperature-indicating label area 76a is made of a thermosensitive non-reversible material, and the humidity label area 76b is made of a moisture-sensitive irreversible material. The irreversible thermosensitive and moisture sensitive materials each have a property of discoloring at a specific temperature and a specific humidity and not returning to the original color once discolored. The temperature display label region 76a includes a plurality of heat sensitive regions having different discoloration temperatures, and the humidity label region 76b includes a plurality of moisture sensitive regions having different color humidity, in this way the user can grasp what kind of temperature environment and humidity environment the reagent kit 100 was put in before use and, for example, it is possible not to use the reagent kit 100 in which the history of temperature and humidity exceeding the usable range is recorded. That is, the third identification label 80 can be used for quality control and the like.

The information of the calibration curve 77 described above also may be recorded in the third identification label 80. In this case, as shown in FIG. 4, information on the calibration curve can be acquired from the third identification label 80 using the reading unit 330 of the sample measuring apparatus 300. In this way the measurement result can be accurately measured by the calibration curve 77 of the third identification label 80 without preparing a calibration curve separately by a user operation. In this case, since it is not necessary to record the information of the calibration curve 77 on the first identification label 30, it is possible to easily secure the data capacity of the first identification label 30 or to minimize the data capacity of the first identification label 30, such that the first identification label 30 can be easily sized to be attached to the container 10.

Specific Configuration Example of Container

Next, a specific configuration example of the container 10 will be described.

Figure 24:
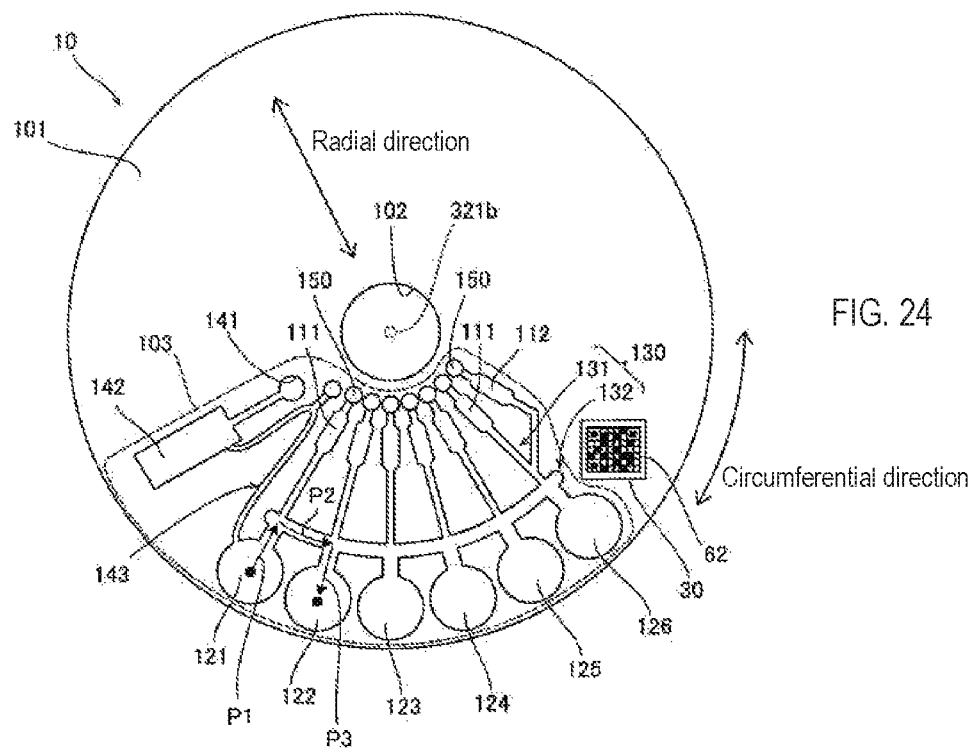
FIG. 24 is a plan view showing a configuration example of a disk type container.

In the example of FIG. 24, the container 10 is a disk type cartridge configured by a plate-like disk-shaped substrate 101. Each part in the container 10 is formed by bonding a recess formed in the substrate 101 and a film (not shown) covering the entire surface including the recess of the substrate 101. The substrate 101 and the film bonded to the substrate 101 are made of a light-transmitting member. The substrate 101 has such a thickness as to facilitate temperature adjustment of the container 10 by a heater 324 described later. For example, the thickness of the substrate 101 is several millimeters, specifically, about 1.2 mm.

The substrate 101 is provided with a sample processing region 103 that includes a hole 102, six housing parts 111, one housing part 112, six chambers 121 to 126, a channel 130, an opening 141, a separation section 142, and a channel 143. The hole 102 penetrates the substrate 101 at the center of the substrate 101. The container 10 is installed in the sample measuring apparatus 300 so that the center of the hole 102 coincides with a rotation shaft 321b described later. Hereinafter, the radial direction and the circumferential direction of a circle centered on the hole 102 are referred to as "radial direction" and "circumferential direction", respectively. Each of the chambers 121 to 126 is a space capable of containing a liquid. The chambers 121 to 126 are arranged in the circumferential direction in the vicinity of the outer periphery of the substrate 101.

The channel 130 includes six radial regions 131 extending in the radial direction and a circumferential region 132 having a circular arcuate shape extending in the circumferential direction. The circumferential region 132 is connected to the six radial regions 131. The six radial regions 131 are connected to the chambers 121 to 126, respectively. The six housing parts 111 are connected to the channel 130 via a radial flow path. The six housing parts 111 are arranged side by side in the radial direction with the corresponding chambers 121 to 126, respectively. The housing part 112 is connected to a flow path that connects the chamber 126 and the housing part 111 mainly via a flow path extending in the radial direction. A total of seven housing parts 111, 112 are arranged on the inner peripheral side of the container 10, and a total of six chambers 121 to 126 are arranged on the outer peripheral side of the container 10.

Each of the housing parts 111 and the housing part 112 accommodates a reagent and is provided with a sealing body 150 on the radially inner top surface. The sealing body 150 is configured so as to be opened by being pressed from above by the sample measuring apparatus 300. The reagent in the housing part 111 does not flow to the channel 130 before the sealing body 150 is unplugged, and the reagent in the housing part 111 flows out to the channel 130 when the sealing body 150 is opened. When the container 10 is rotated, the reagent moves to the corresponding chambers 121 to 126 by centrifugal force.

A sample is injected into the opening 141. The sample is a blood sample of whole blood taken from the subject. The blood sample is injected into the separation section 142 through the opening 141. The separating section 142 separates the injected blood sample into blood cells and plasma. The plasma separated by the separation section 142 moves to the channel 143. When the container 10 is rotated, the plasma in the channel 143 moves to the chamber 121 by centrifugal force. In this way a predetermined amount of plasma is transferred to the chamber 121.

A reagent containing magnetic particles is enclosed in the chamber 121. The sample measuring apparatus 300 sequentially transfers the magnetic particles to a plurality of chambers, thereby causing the magnetic particles to carry the test substance and the labeling substance, and detects the test substance based on the labeling substance. That is, the magnetic particles carrying the test substance are moved in the radial direction by the magnetic force. As a result, the magnetic particles are radially moved by the magnetic force between the inside of the chamber 121 and the arcuate circumferential region 132 of the channel 130. As the container 10 is rotated, the magnetic particles move in the circumferential direction within the arcuate circumferential region 132. The magnetic particles carrying the test substance are moved to the chambers 121 to 126 by the combination of the radial movement via the effect of the magnetic force and the circumferential movement by the rotation, and the processing using the reagent is performed in each of the chambers 121 to 126. Finally, the magnetic particles carrying the test substance and the labeling substance are moved to the chamber 126, and the labeling substance is detected by the sample measuring apparatus 300, whereby the measurement is performed.

Note that the sample processing region 103 in the example of FIG. 24 is formed only in a third of the substrate 101. However, the present invention is not limited to this configuration, and two sample processing regions 103 may be formed in the remaining two-thirds region of the substrate 101, and three sample processing regions 103 may be provided on the substrate 101. Note that one sample processing region 103 may be formed over a region larger than one-third of the region of the substrate 101.

In the case where a plurality of sample processing regions 103 are provided, each sample processing region 103 may be a sample processing region 103 for the same measurement item or a sample processing region 103 for different measurement items. When a plurality of sample processing regions 103 of the same measurement item are provided, measurement of the same measurement item can be performed a plurality of times in one container 10. When sample processing regions 103 of different measurement items are provided, it is possible to measure a plurality of items with one container 10 for the same sample.

The first identification label 30 is provided in the container 10. The first identification label 30 includes a multidimensional code 62.

Figure 25:
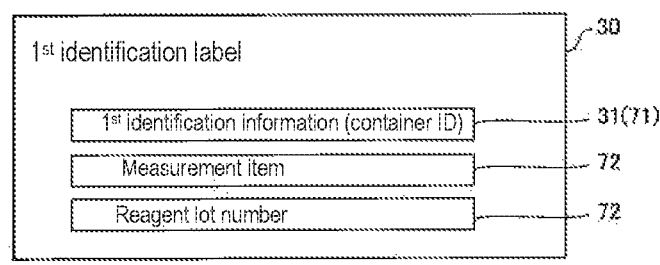
FIG. 25 is a diagram showing information recorded on a first identification label in FIG. 24.

As shown in FIG. 25, the first identification label 30 includes at least the first identification information 31. The first identification information 31 is a container ID of the container 10 as information 71 for identifying the container 10. The first identification label 30 includes the lot number of the reagent as the measurement-related information 72. Measurement related information 72 may include, for example, information for specifying the type of reagent, expiration date of the reagent, and the like. The first identification label 30 includes information on measurement items as measurement related information 72. For example, the information of the measurement item may be a code indicating the measurement item, or the name of the measurement item itself. The procedure of the measurement operation using the reagent, the individual operation time, the operation content, the temperature setting, and the like are decided according to the measurement item. For example, the measurement operation corresponding to the measurement item is preset in the sample measuring apparatus 300. The measurement operation corresponding to the measurement item is determined by the measurement item recorded on the first identification label 30. In other words, the information of the measurement item is information for specifying the type of the container 10. In this way it is possible to determine the measurement operation using the reagent of the container 10 based on the measurement item for the sample. In particular, when the sample measuring apparatus 300 is capable of measuring a plurality of types of measurement items with a plurality of types of containers 10, measurement can be performed by an appropriate measurement operation according to the measurement item.

Specific Configuration Example of Sample Measuring Apparatus

Figure 26:
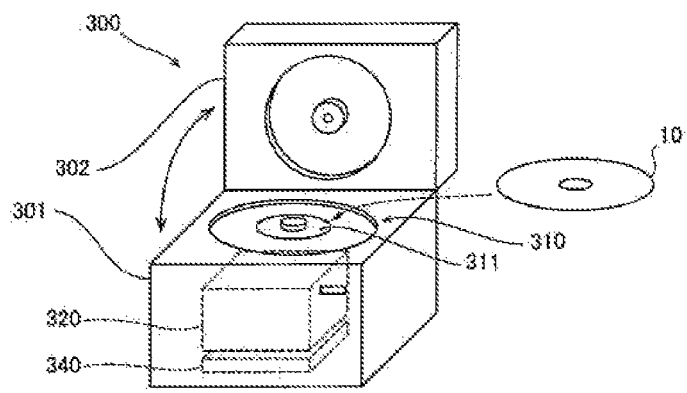
FIG. 26 is a perspective view showing a state in which the lid is opened in the configuration example of the sample measuring apparatus.
Figure 27:
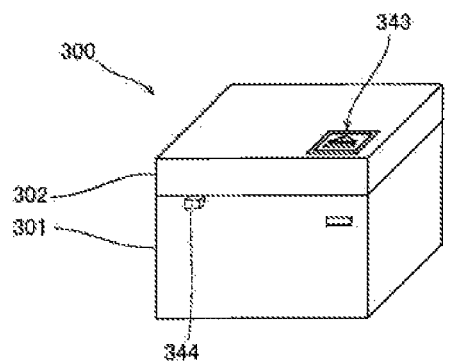
FIG. 27 is a perspective view showing a state in which the lid is closed in the configuration example of the sample measuring apparatus.
Figure 28:
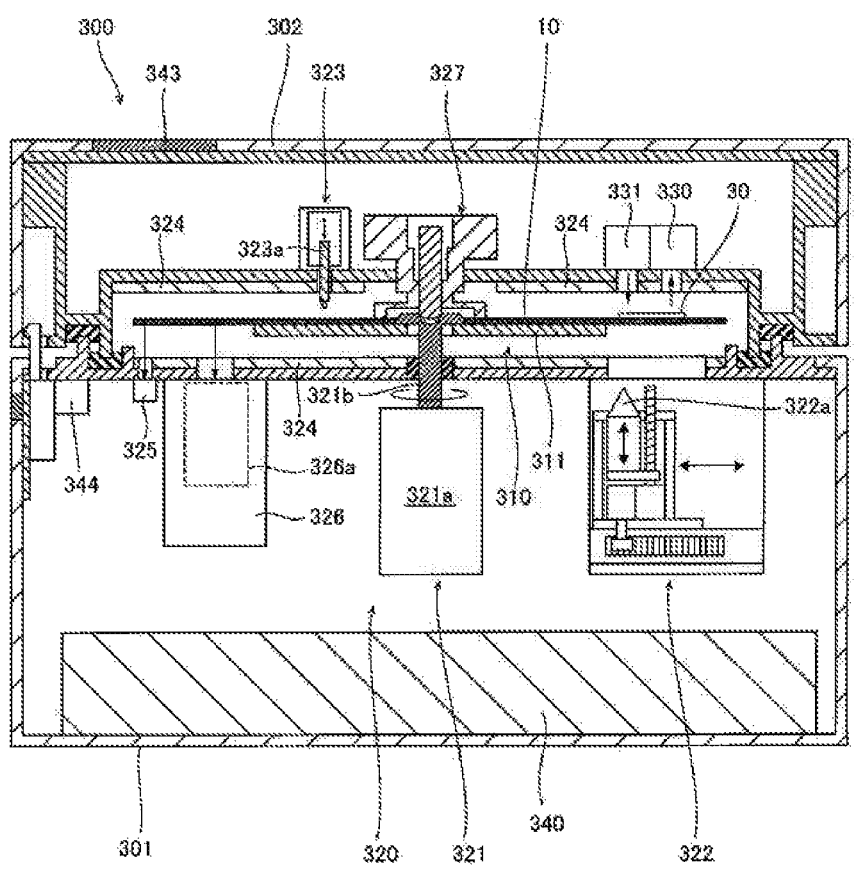
FIG. 28 is a schematic vertical cross sectional view showing a configuration example of a sample measuring apparatus.

FIG. 26 to FIG. 28 show a specific configuration example of the sample measuring apparatus 300 using the container 10.

In the examples shown in FIGS. 26 to 28, the sample measuring apparatus 300 is an immunoassay apparatus that detects a test substance in a sample using an antigen-antibody reaction, and measures the test substance based on the detection result. The sample measuring apparatus 300 performs measurements using the container 10 which is a disk-type cartridge.

The sample measuring apparatus 300 includes a main body 301 and a lid 302. The lid 302 is provided so as to cover substantially the entire upper surface portion of the main body 301. An arrangement portion 310 on which the container 10 is disposed is provided on the upper surface of the main body 301. The lid 302 rotates with respect to the main body 301, and is provided so as to be opened and closed in a state in which the arrangement portion 310 shown in FIG. 26 is opened and a state in which the lid 302 covers the arrangement portion 310 shown in FIG. 27.

Note that the sample measuring apparatus 300 in FIGS. 26 and 27 is a displayless apparatus having no display screen. That is, the sample measuring apparatus 300 is configured so as not to perform operation input using the user interface by itself. The sample measuring apparatus 300 acquires information necessary for starting the measurement by reading the information recorded on the first identification label 30 of the container 10. Therefore, complicated input operations via the user interface can be omitted, and erroneous input of information by the user can be suppressed.

Internal Structure of Sample Measuring Apparatus

The internal structure of the sample measuring apparatus 300 will be described below with reference to FIG. 28.

The sample measuring apparatus 300 includes a measuring unit 320 for measuring a sample using the container 10 disposed in the arrangement portion 310.

The arrangement portion 310 (see FIG. 26) configures the upper surface portion of the main body 301 which is covered openably and closably by the cover 302. The arrangement portion 310 includes a support member 311 that supports the container 10 from below. The support member 311 is configured by, for example, a turn table.

In the example of FIG. 28, the measuring unit 320 includes a rotation driving unit 321, a magnet driving unit 322, a plug opening unit 323, a heater 324, a temperature sensor 325, and a light detection unit 326.

The rotation driving unit 321 is a mechanism for rotating the container 10. The rotation driving unit 321 includes a motor 321a and a rotation shaft 321b. The rotation driving unit 321 drives the motor 321a to rotate the container 10 set on the support member 311 around the rotation shaft 321b that coincides with the center of the hole 102. The rotation driving unit 321 centrifugally separates the blood sample by rotation, moves the reagent to each of the chambers 121 to 126, stirs the reagent and the sample, and transfers the magnetic particles between the chambers 121 to 126 in the circumferential direction.

The magnet driving unit 322 includes a magnet 322a and has a function of moving the magnetic particles inside the container 10 in the radial direction. The magnet driving unit 322 is disposed below the arrangement portion 310 and moves the magnet 322a in the radial direction at least in a range (refer to FIG. 24) between the chambers 121 to 126 and the circumferential area 132 of the channel 130.

The plug opening unit 323 unplugs the sealing body 150 by a pin member 323a capable of advancing and retracting toward and away from the container 10 and which protrudes from above the container 10 disposed in the arrangement portion 310 so as to be in contact with the container 10 and press the container 10 from above to unplug the sealing body 150 (refer to FIG. 24). After opening, the opening unit 323 moves the pin member 323a away from the container 10 to a retracted position where it is not in contact.

The heater 324 is provided at a position immediately below the container 10 arranged in the arrangement portion 310 and at a position immediately above the container 10. The heater 324 heats the sample accommodated in the chambers 121 to 126 to a predetermined reaction temperature to accelerate the reaction between the sample and the reagent. The temperature sensor 325 detects the temperature of the container 10 by infrared rays.

The light detection unit 326 is provided with a light receiving part at a position opposite to the container 10 arranged in the arrangement portion 310 via an opening formed in the main body 301. In this way the light detection unit 326 detects the light generated from the inside of the chamber 126 from the light receiving unit. The light detection unit 326 includes a photodetector 326 a such as a photomultiplier tube, a photoelectric tube, a photodiode, or the like. The photodetector 326a outputs a pulse waveform corresponding to photon reception. The light detection unit 326 has an internal circuit, counts photons at constant intervals based on the output signal of the photodetector 326a, and outputs a count value.

The sample measuring apparatus 300 includes a damper 327, a reading unit 330, and an illumination unit 331.

The damper 327 rotatably supports the center portion of the upper surface of the container 10 installed on the support member 311 with the lid 302 in a closed state. The container 10 is supported sandwiched between the support member 311 and the damper 327.

In the example of FIG. 28, the reading unit 330 is an imaging unit that images the multidimensional code 62 of the first identification label 30 (see FIG. 24). The reading unit 330 directly faces the upper surface of the container 10 via a hole provided in the lid 302. Similarly, the illumination unit 331 directly faces the upper surface of the container 10 via a hole provided in the lid 302. The reading unit 330 includes, for example, a CCD image sensor, a CMOS image sensor, and the like. The illumination unit 331 is configured by, for example, a light emitting diode, and generates illumination light during imaging. The reading unit 330 images the first identification label 30in a state in which the container 10 is rotated in the circumferential direction and the first identification label 30 is disposed in the imaging field of view. Information including the first identification information 31 is read from the captured image of the multidimensional code 62.

Figure 29:
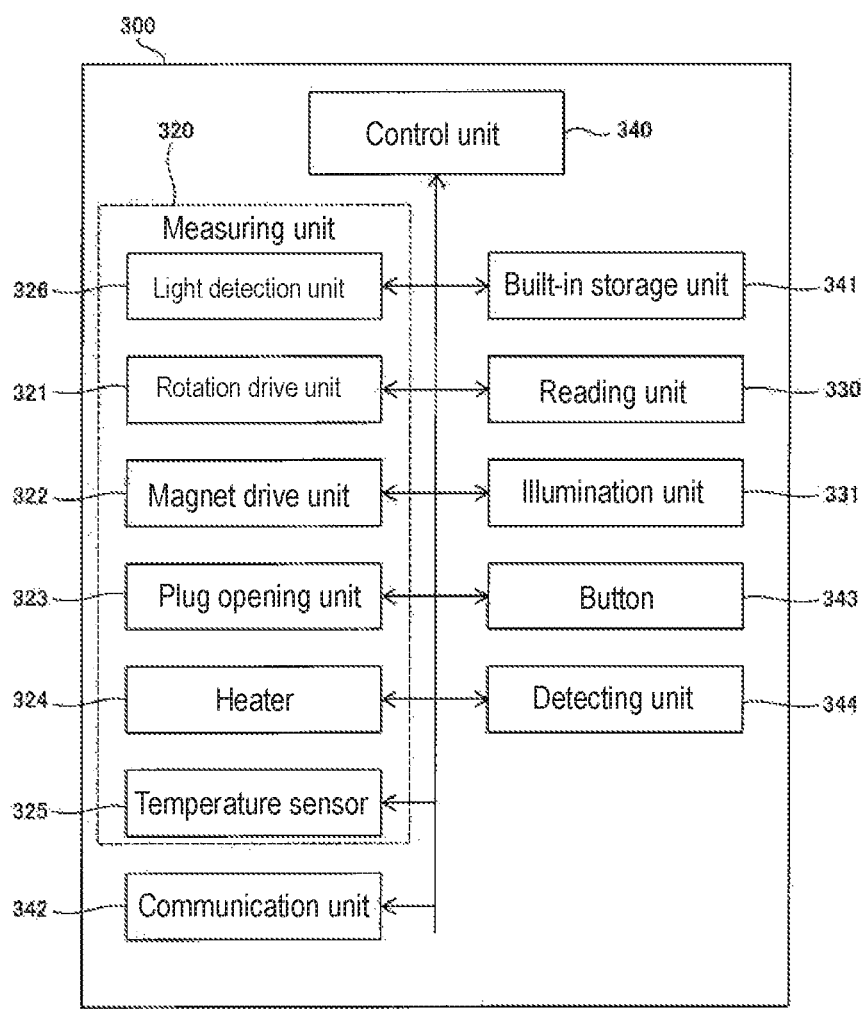
FIG. 29 is a block diagram showing a control configuration example of a sample measuring apparatus.

FIG. 29 shows a control configuration of the sample measuring apparatus 300.

The sample measuring apparatus 300 includes a control unit 340. The control unit 340 includes, for example, a processor and a memory. The processor is configured by, for example, a CPU, an MPU, or the like. The memory is composed of, for example, a ROM and a RAM. The control unit 340 receives signals from each unit of the sample measuring apparatus 300 and controls each unit of the sample measuring apparatus 300.

The sample measuring apparatus 300 includes an internal storage unit 341. At least the measurement result data 50 in which the first identification information 31 is associated with the measurement result 51 is stored in the built-in storage unit 341. The built-in storage unit 341 is composed of, for example, a flash memory, a hard disk, or the like.

Figure 30:
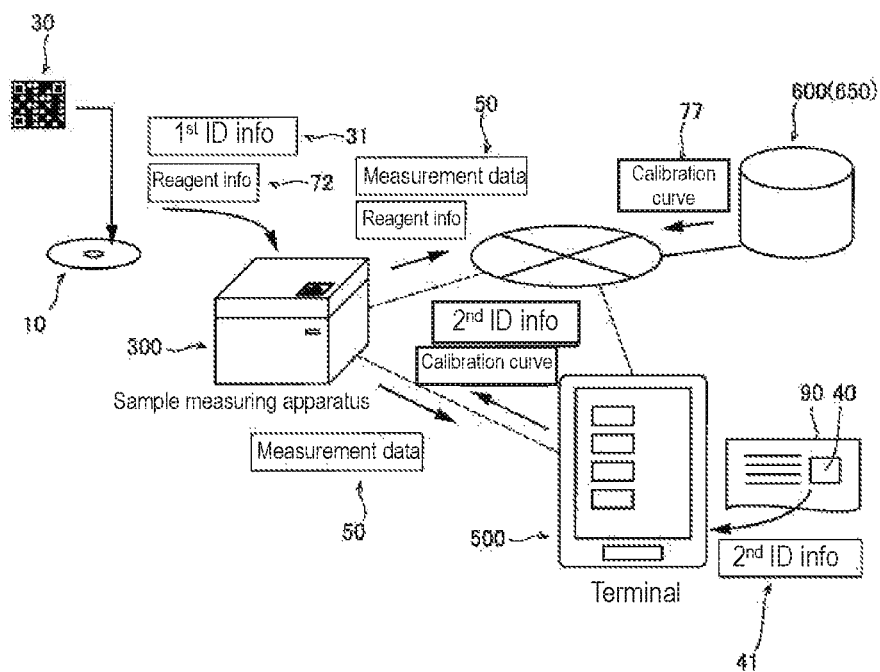
FIG. 30 is a diagram showing a network relating to a sample measuring apparatus.

The sample measuring apparatus 300 includes a communication unit 342. The communication unit 342 is capable of transmitting information to external devices and receiving information from external devices. The communication unit 342 includes, for example, a communication module, an interface for external connection, and the like. As shown in FIG. 30, the communication unit 342 is capable of communicating with the terminal 500 and communication with the servers 600 and 650 via a network by wired or wireless communication. The communication unit 342 may be capable of communicating using a plurality of types of communication methods. The connection to the network is, for example, a wired LAN, a wireless LAN, or the like. The connection with the terminal 500 may be performed by wired LAN, wireless LAN, Bluetooth (registered trademark), another NFC (short range wireless communication), or the like. Connection with the terminal 500 may be performed by an interface for external connection such as USB. The server 600 is a server that manages the measurement result data 50, and the server 650 is a server that manages reagent information including calibration curves.

In addition, the sample measuring apparatus 300 shown in FIG. 29 includes a button 343 (see FIG. 27) for accepting a user operation at the time of opening the lid 302, and a detecting unit 344 (see FIG. 27) for detecting the opening and closing of the lid 302.

Description of Operation of Sample Measuring Apparatus

Next, the operation of the sample measuring apparatus 300 will be described with reference to FIG. 31. In the following description, the structure of the sample measuring apparatus 300 will be described referring to FIGS. 26 to 30. For the structure of the container 10, refer to FIG. 24.

First, the user injects the blood sample collected from the subject through the opening 141 of the container 10. A measurement example of hepatitis B surface antigen (HBsAg) is shown as an example of measurement items of the container 10. The test substance in the blood sample contains an antigen. The antigen is hepatitis B surface antigen (HBsAg). The test substance may be one or more of an antigen, an antibody, or a protein. Measurement items may be prostate specific antigen (PSA), thyroid stimulating hormone (TSH), thyroid hormone (FT4) and the like.

Predetermined reagents are contained in the housing parts 111 and 112 of the container 10 and the chamber 121 in advance. Specifically, the R1 reagent is accommodated in the housing part 111 positioned in the radial direction of the chamber 121. The R2 reagent is accommodated in the chamber 121. R3 reagent is contained in the housing part 111 positioned in the radial direction of the chamber 122. A cleaning liquid is contained in the housing part 111 positioned in the radial direction of the chambers 123 to 125. R4 reagent is contained in the housing part 111 positioned in the radial direction of the chamber 126. R5 reagent is contained in the housing part 112.

Figure 31:
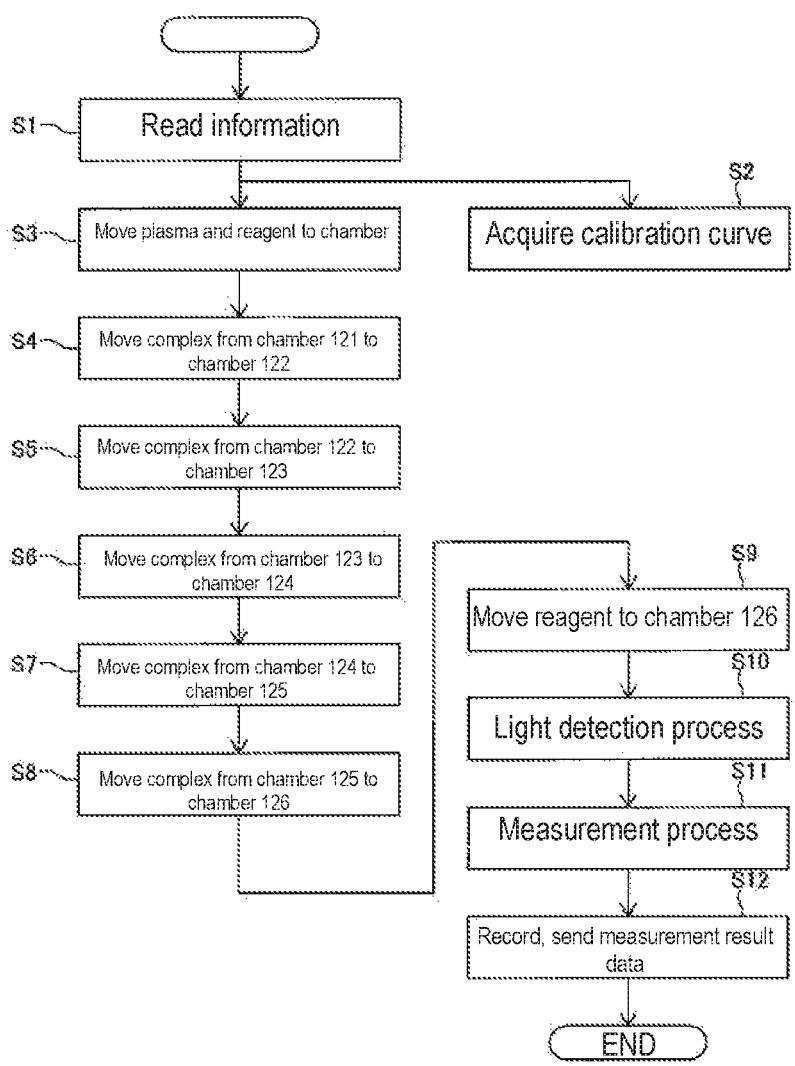
FIG. 31 is a flowchart for explaining the measurement operation of the sample measuring apparatus.

In step S1 of FIG. 31, the control unit 340 executes a reading operation of the first identification label 30 of the container 10 installed by the user. That is, the control unit 340 rotates the container 10 and executes the photographic operation by the reading unit 330. The control unit 340 acquires the first identification information 31 recorded in the first identification label 30 (see FIG. 25) based on the captured image, the lot number of the reagent is acquired as the measurement-related information 72, and information on the measurement item is acquired.

After step S3, the control unit 340 starts the measurement operation by the measuring unit 320. In the measurement operation, the reaction time and the like between the sample and the reagent vary depending on the measurement item. Therefore, the sample measuring apparatus 300 stores the measurement operation pattern for each measurement item in the built-in storage unit 341. The control unit 340 controls the operation of the measuring unit 320 by selecting a measurement operation pattern corresponding to the measurement item based on the measurement item information read by the reading unit 330.

In step S2, the control unit 340 acquires the calibration curve 77. Here, the control unit 340 transmits the lot number of the reagent as the measurement-related information 72 to the terminal 500 or the server 650 (see FIG. 30) by the communication unit 342, specifies the calibration curve 77 of the measurement using the reagent specified by the lot number, and requests data transmission of the calibration curve 77. The control unit 340 acquires the specified calibration curve 77 via the communication unit 342 as a response from the terminal 500 or the server 650. Note that the acquisition process of the calibration curve 77 in step S2 may be performed at any timing insofar as it is performed from information reading to measurement processing in step S11 described later.

In step S3, the control unit 340 transfers the plasma and the reagent to the chamber. Specifically, the control unit 340 aligns the container 10 with the rotation driving unit 321, drives the plug opening unit 323, and opens the respective sealing bodies 150 of the six housing parts 111. The control unit 340 rotates the container 10 by the rotation driving unit 321 and transfers the plasma from the channel 143 to the chamber 121 by centrifugal force, and transfers the reagents accommodated in the six housing parts 111 to the chambers 121 to 126. In this way in the chamber 121, plasma, R1 reagent, and R2 reagent are mixed. The R3 reagent is transferred to the chamber 122, the cleaning liquid is transferred to the chambers 123 to 125, and the R4 reagent is transferred to the chamber 126.

In step S3, when the transfer of the plasma and the reagent is completed, the control unit 340 also intermittently rotationally drives the container 10 by the rotation driving unit 321 and performs an agitation process. In this way the liquid in the chambers 121 to 126 is stirred. Such an agitation process is performed not only in step S3, but also in steps S4 to S9 in the same manner after the transfer process.

Here, the R1 reagent contains a capture substance that binds to the test substance. The capture substance includes, for example, an antibody that binds to the test substance. The antibody is, for example, a biotin-conjugated HBs monoclonal antibody. The R2 reagent contains magnetic particles in the liquid component. Magnetic particles are, for example, streptavidin-bound magnetic particles whose surface is coated with avidin. The test substance and the R1 reagent are bound by the antigen-antibody reaction when the plasma, the R1 reagent, and the R2 reagent are mixed and agitated in step S12. Then, due to the reaction between the antigen-antibody reactant and the magnetic particles, the test substance bound to the capture substance of the R1 reagent is bound to the magnetic particle via the capture substance. As a result, a complex in a state where the test substance and magnetic particles are bound is generated.

Next, in step S4, the control unit 340 transfers the complex in the chamber 121 from the chamber 121 to the chamber 122.

Upon transfer of the complex, the controller 340 drives the magnet driver 322 to bring the magnet 322a close to the container 10 to collect the complex that extends into the chamber 121. The control unit 340 combines the radial movement of the magnet 322a driven by the magnet driving unit 322 and the circumferential movement of the container unit 10 by the rotation driving unit 321 to move the complex inward in the radial direction of the path P1 in FIG. 24 along the channel 130 to the chamber 122 in the order of the circumferential movement of the path P2 and the radial outward movement of the path P3. The control unit 340 performs an agitation process after moving the complex. Note that since the movement of the complex to each of the chambers 123 to 126 is carried out by the same method, a detailed description thereof will be omitted.

In this way the complex generated in the chamber 121 and the R3 reagent are mixed in the chamber 122. Here, the R3 reagent contains a labeling substance. The labeling substance includes a capture substance that specifically binds to the test substance, and a label. For example, the labeling substance is a labeled antibody in which an antibody is used as a capture substance. In step S4, when the complex generated in the chamber 121 and the R3 reagent are mixed and agitated, the complex generated in the chamber 121 reacts with the labeled antibody contained in the R3 reagent. As a result, a complex is produced in which the test substance, the capture antibody, the magnetic particles, and the labeled antibody are bound.

In step S5, the control unit 340 transfers the complex in the chamber 122 from the chamber 122 to the chamber 123. In this way the complex generated in the chamber 122 and the cleaning liquid are mixed in the chamber 123. In step S5, when the complex generated in the chamber 122 and the cleaning liquid are mixed and agitated, the complex and the unreacted substance are separated in the chamber 123. That is, unreacted substances are removed by cleaning in the chamber 123.

In step S6, the control unit 340 transfers the complex in the chamber 123 from the chamber 123 to the chamber 124. In this way the complex generated in the chamber 122 and the cleaning liquid are mixed in the chamber 123. Unreacted substances also are removed by cleaning in the chamber 124.

In step S7, the control unit 340 transfers the complex in the chamber 124 from the chamber 124 to the chamber 125. In this way the complex generated in the chamber 122 and the cleaning liquid are mixed in the chamber 125. Unreacted substances also are removed by cleaning in the chamber 125.

In step S8, the control unit 340 transfers the complex in the chamber 125 from the chamber 125 to the chamber 126. In this way the complex generated in the chamber 122 and the R4 reagent are mixed in the chamber 126. Here, the R4 reagent is a reagent for dispersing the complex generated in the chamber 122. The R4 reagent is, for example, a buffer solution. In step S8, when the complex generated in the chamber 122 and the R4 reagent are mixed and agitated, the complex generated in the chamber 122 is dispersed.

In step S9, the control unit 340 transfers the R5 reagent to the chamber 126. Specifically, the control unit 340 aligns the container 10 with the rotation driving unit 321, drives the opening plug unit 323, and opens the sealing body 150 of the housing part 112. The control unit 340 rotates the container 10 by the rotation driving unit 321 and transfers the R5 reagent accommodated in the housing part 112 to the chamber 126 by centrifugal force. In this way the R5 reagent is further mixed with the mixed solution generated in step S8 in the chamber 126.

Here, the R5 reagent is a luminescent reagent comprising a luminescent substrate that produces light upon reaction with a labeled antibody bound to the complex. In step S9, a sample is prepared when the mixed solution produced in step S8 and the additionally transferred R5 reagent are mixed and stirred. This sample chemiluminesces by reacting the labeling substance bound to the complex with the luminescent substrate.

In step S10, the control unit 340 positions the chamber 126 right above the light receiving unit of the light detection unit 326 by the rotation driving unit 321, and detects the light generated from the chamber 126 by the light detection unit 326. In step S11, the control unit 340 performs measurement process related to immunity based on the light detected by the light detection unit 326. The light detection unit 326 counts photons at regular intervals and outputs a count value. The control unit 340 measures the presence/absence and quantity of the test substance and generates the measurement result 51 based on the count value output from the light detection unit 326 and the calibration curve 77 acquired in step S2.

When the measurement result 51 is obtained, the control unit 1340 associates the container ID as the first identification information 31 with the measurement execution date and time at the time of measurement in the measurement result 51, and stores the measurement result as the measurement result data 50 in the storage unit 341. The control unit 340 also transmits the measurement result data 50 to the server 600 by the communication unit 342.

In this way the measurement operation of the sample measuring apparatus 300 is completed. As shown in FIG. 30, when the measurement result data 50 is recorded and transmitted, the user can acquire the measurement result data 50 from the terminal 500 or server 600 using the second identification information 41 recorded in the second identification label 40.

Note that in the above measurement operation, chemiluminescence is light emitted utilizing energy from a chemical reaction, for example, molecules are excited by a chemical reaction, and light is emitted when the molecules return from the excited state to the ground state. Chemiluminescence can be generated, for example, by reaction between an enzyme and a substrate, by generating an electrochemical stimulus to a labeling substance, or can be generated based on the LOCI method (Luminescent Oxygen Channeling Immunoassay). In the first embodiment, any chemiluminescence may be performed. When a light of a predetermined wavelength is irradiated, a substance excited with fluorescence and a test substance may be combined to constitute a complex. In this case, a light source for irradiating light to the chamber 126 is arranged. The photodetector detects fluorescence excited from a substance bound to the complex by light from the light source.

Note that the magnetic particles may be particles that contain a magnetic material as a base material, and may be used for ordinary immunoassay. For example, magnetic particles using $Fe_2O_3$ and/or $Fe_3O_4$, cobalt, nickel, filite, magnetite or the like as the base material can be used. The magnetic particles also may be coated with a binding substance for binding to the test substance or may be bound to the test substance via a capture substance for binding the magnetic particles and the test substance. The capture substances are magnetic particles and antigens or antibodies which mutually bind to the test substance.

The capture substance is not particularly limited insofar as it specifically binds to the test substance. For example, a capture substance may bind to a test substance by an antigen-antibody reaction. More specifically, the capture substance may be an antibody, but when the test substance is an antibody, the capture substance may be an antigen of the antibody. When the test substance is a nucleic acid, the capture substance may be a nucleic acid complementary to the test substance. As the label contained in the labeling substance, for example, an enzyme, a fluorescent substance, a radioactive isotope and the like can be mentioned. Examples of the enzyme include alkaline phosphatase (ALP), peroxidase, glucose oxidase, tyrosinase, acid phosphatase and the like. When performing electrochemiluminescence as the chemiluminescence, the label is not particularly limited insofar as it is a substance that emits light by electrochemical stimulation, for example, a ruthenium complex can be mentioned. As fluorescent substances, fluorescein isothiocyanate (FITC), green fluorescent protein (GFP), luciferin and the like can be used. As the radioactive isotope, 125I, 14C, 32P and the like can be used.

When the label is an enzyme, a known luminescent substrate may be appropriately selected according to the enzyme to be used as the luminescent substrate for the enzyme. For example, as a luminescent substrate when alkaline phosphatase is used as an enzyme, CDP-Star (registered trademark), (4-chloro-3-(methoxyspiro [1,2-dioxetane-3,2'-(5'-chloro)tricyc [3.3.1.13,7] decane]-4-yl) phenyl phosphate), CSPD® (3-(4-methoxyspiro [1,2-dioxetane-3, 2-(5'-chloro) tricyc [3.3.1.13,7] decane]-4-yl) phenyl phosphate); chemiluminescent substrates such as p-nitrophenyl phosphate, 5-bromo-4-chloro-3-indolyl phosphate (BCIP), 4-nitro blue tetrazolium chloride (NBT), iodonitrotetrazolium (INT); 4-methyl umbellyphenyl phosphate (4 MUP); chromogenic substrates such as 5-bromo-4-chloro -3-indolyl phosphate (BCIP), 5-bromo-6-chloro-indolyl phosphate disodium and p-nitrophenylphosphorus.

Modification of Sample Measuring Apparatus

Figure 32:
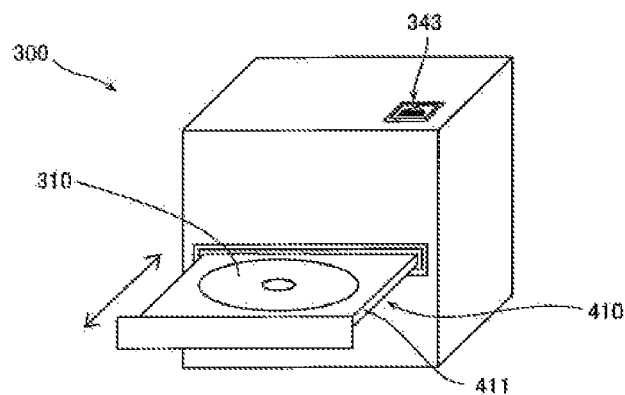
FIG. 32 is a diagram showing another configuration example of a sample measuring apparatus.

Although an example of the sample measuring apparatus 300 of the type in which the lid 302 is opened and closed has been shown in FIGS. 26 and 27, in the sample measuring apparatus 300 in FIG. 32, a loader 410 is provided in place of the lid 302 to move the arrangement portion 310 into and out of the sample measuring apparatus 300. The loader 410 includes a tray 411 provided with an arrangement unit 310. The tray 411 moves to a projecting position outside the sample measuring apparatus 300 and a measuring position in the sample measuring apparatus 300. At the projecting position, the user can place or remove the container 10 with respect to the arrangement portion 310 of the tray 411. At the measurement position, reading of information recorded on the first identification label 30 can be read by the reading unit 330, and measurement operations can be executed on the container 10 on the placement unit 310 by the measuring unit 320.

Modification Example of Container

Figure 33:
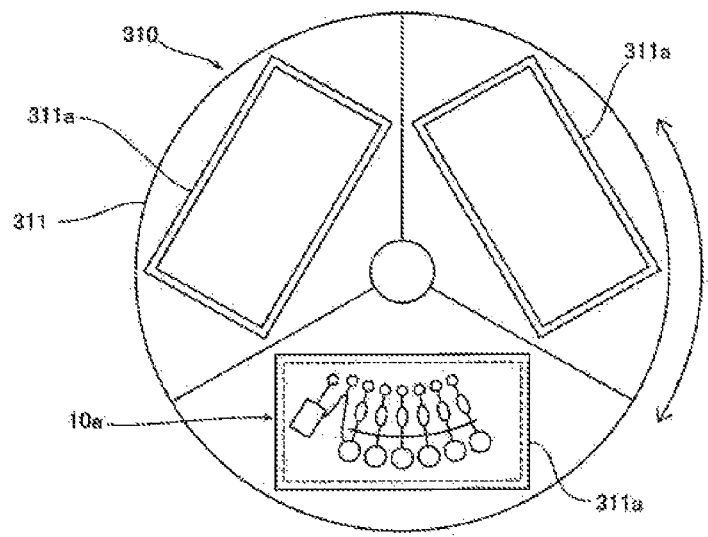
FIG. 33 is a view showing a first modified example of a container.

Although an example of using the disk type container 10 is shown in FIG. 24, in FIG. 33 a rectangular plate type container 10*a* is used instead of the disk type container 10. The other configuration is the same as the specific configuration example of the first embodiment.

A rectangular arrangement region 311*a* corresponding to the container 10*a* is provided on the support member 311 of the arrangement portion 310. In FIG. 33, three arrangement regions 311*a* are provided along the circumferential direction of the disk-shaped support member 311. The container 10*a* is provided with a chamber and a channel similar to the container 10 shown in FIG. 24. As in FIG. 24, the container 10 may be provided with a first identification label 30 by a user, or may be provided with a first identification label 30 in advance. The containers 10 arranged in the three placement regions 311*a* may measure the same measurement item or measure different measurement items. In the example of FIG. 33, the sample measuring apparatus 300 can perform the measuring operations simultaneously and in parallel on up to three containers 10.

Figure 34:
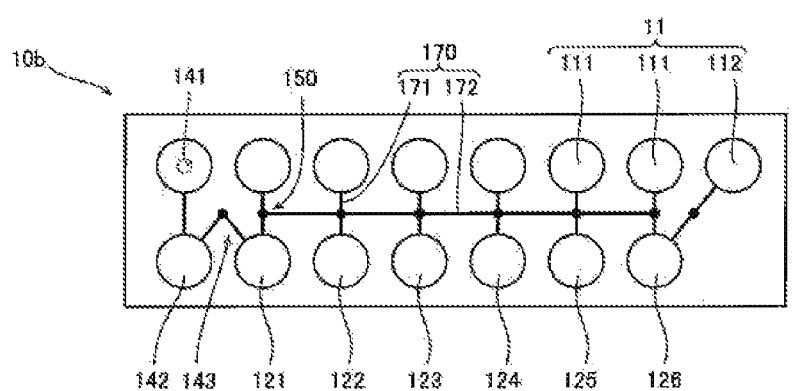
FIG. 34 is a view showing a second modified example of a container.

FIG. 34 shows an example in which the container 10*b* is a well plate. The other configuration is the same as the specific configuration example of the first embodiment.

The container 10*b* includes an opening 141 for injecting a sample, a housing part 11 for accommodating a reagent, chambers 121 to 126, and a channel 170. These housing parts and chambers are configured by wells formed in the plate member. The channel 170 is provided with a sealing body 150. The container 10*b* can be arranged in the arrangement portion 310 similar to FIG. 33. The channel 171 connecting the housing part 11 and the chambers 121 to 126 mainly extends in the radial direction and the channel 172 connecting the channels 171 mainly extends in the circumferential direction in a state of being set in the arrangement region 311*a* of the support member 311. Therefore, the test substance combined with the magnetic particles can be moved to the respective chambers 121 to 126 by combining the rotation of the container 10 and the movement of the magnet 322*a* in the radial direction.

Figure 35:
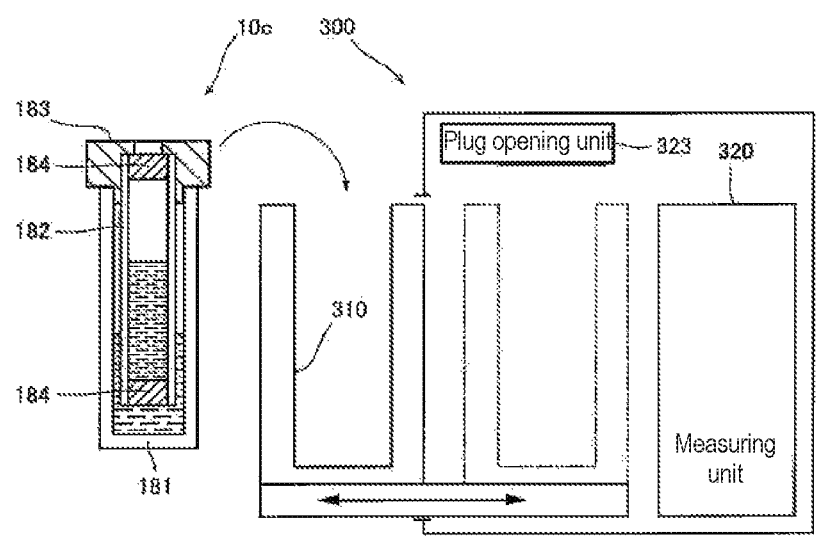
FIG. 35 is a view showing a third modified example of a container.

FIG. 35 shows an example in which the container 10*c* is a tubular member such as a cuvette.

In the example of FIG. 35, the container 10*c* has a nested structure of a tubular outer housing part 181 and a tubular inner housing part 182 arranged inside the outer housing part 181. The outer housing part 181 is a tubular container with a closed bottom and an open upper portion, and the sample is injected through the opening. The inner housing part 182 is a tube with both upper and lower ends opened, and the upper and lower openings are closed by the sealing bodies 184. Reagents are stored in advance in the sealed housing part 182. The upper end portion of the housing part 182 can be attached to the cap 183. The cap 183 is attached to the opening of the housing part 181 and blocks the opening. In the center portion of the cap 183, a hole for exposing the sealing body 184 at the upper portion of the housing part 182 is provided.

The measuring unit 320 presses the upper sealing body 184 through the hole of the cap 183 by the plug opening unit 323, whereby the lower sealing body 184 is removed from the housing part 182. The lower sealing body 184 falls into the housing part 181. As a result, the reagent accommodated in the housing part 182 and the sample accommodated in the housing part 181 are mixed. In the example of FIG. 35, the measuring unit 320 agitates the sample and the reagent contained in the housing part 181 by mechanically vibrating the container 10*c*, applying a temporally changing magnetic field, or the like to elicit a reaction. The measurement unit 320 detects the test substance by detecting luminescence resulting from the reaction, fluorescence due to irradiation with excitation light, change in color or turbidity, and the like.

The user injects the blood sample into the housing part 181 and covers the container 10*c* by covering with the cap 183 to which the housing part 182 is attached. The user places the container 10*c* in the arrangement portion 310. Then, the reading unit 330 reads information from the first identification label 30. The control unit 340 starts the measurement by the measuring unit 320. In the example of FIG. 35, the first identification label 30 (not shown) can be applied to, for example, the outer peripheral surface of the outer housing part 181.

Modification of Second Identification Label

Figure 36:
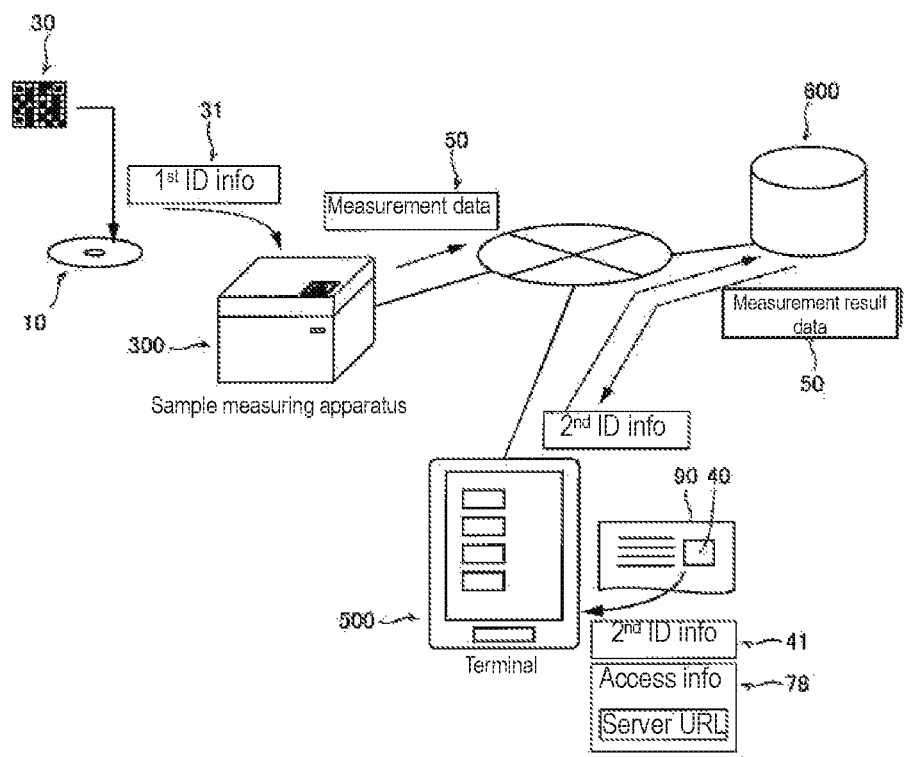
FIG. 36 is a diagram showing an example in which the second identification label includes information for accessing a server.

In the example of FIG. 36, the second identification label 40 includes, in addition to the second identification information 41, information 78 for accessing the server 600 that manages measurement results using the container 10. The information 78 for accessing the server 600 includes address information such as URL or IP address of the server 600 on a network such as the Internet. The user operates the terminal 500 to read the information from the second identification label 40 so that the terminal 500 acquires the second identification information 41 and the information 78 for accessing the server 600. Therefore, the terminal 500 can immediately access the server 600 which manages the measurement results by the information 78 read from the second identification label 40 without the user manually entering the URL of the server 600 into the terminal 500. The terminal 500 transmits the second identification information 41 to the server 600 and requests measurement result data 50 including the first identification information 31 associated with the second identification information 41. As a response to the request, the terminal 500 can acquire the measurement result data 50 including the first identification information 31 corresponding to the second identification information 41.

In this way, in the configuration example of FIG. 36, the server 600 can be accessed immediately by the user merely reading information from the second identification label 40 by recording the information 78 for accessing the server 600 in the second identification label 40. Then, the measurement result data 50 recorded in the server 600 can be specified and acquired by using the second identification information 41 associated with the first identification information 31.

Note that, in addition to the address information of the server 600, the information 78 for accessing the server 600 may include authentication information for the server 600, for example. The information 78 for accessing the server 600 is required for the terminal 500 to access the server 600 and acquire the measurement result data 50 including the first identification information 31 associated with the second identification information 41 from the server 600, and may include information other than the address information and the authentication information.

Second Embodiment

A second embodiment will be described below with reference to FIG. 37. The second embodiment shows an example of a measurement result management data structure including the first identification information 31 and the second identification information 41 of the first embodiment. Note that, in the second embodiment, descriptions of configurations similar to those of the first embodiment are omitted.

In the system 700 constituted by the above-described sample measuring apparatus 300, the server 600 for managing the measurement result, and the terminal 500 used by the user for handling the information of the subject of the second embodiment, the reagent kit 100 is used to manage the measurement result data 50 obtained by using the data structure 800 for measurement result management. Note that the server 600 for managing the measurement result is not an electronic medical chart system managed and operated by the user, but rather is a general-purpose external service that merely accumulates the measurement result data 50. The server 600 is, for example, a server used for providing a PHR (Personal Health Record) service. As an external service, the server 600 does not have a function associating measurement result data 50 accumulated by the server 600 with subject information managed by a specific user in cooperation with a terminal that manages the subject information.

Figure 37:
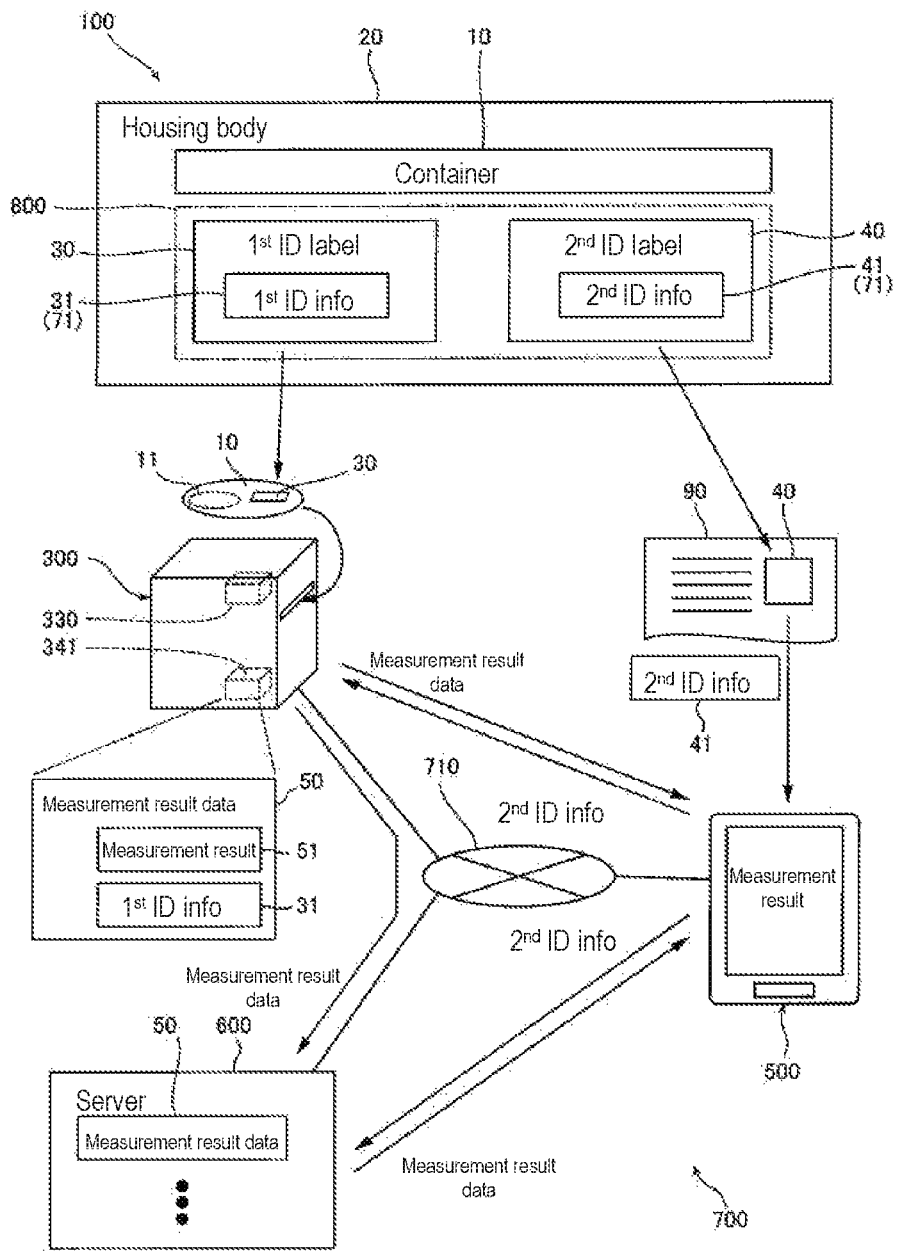
FIG. 37 is a schematic diagram for describing a data structure according to a second embodiment.

In the example of FIG. 37, the sample measuring apparatus 300 and the terminal 500 and the server 600 for managing the measurement result are connected via a network 710. The sample measuring apparatus 300 and the terminal 500 may be connected via the network 710 or may be connected via a wired connection such as a USB connection or short range wireless communication capable of direct communication such as Bluetooth or the like without going through the network 710. The terminal 500 may communicate with at least one of the sample measuring apparatus 300 and the server 600.

The data structure includes the first identification information 31 recorded in the first identification label 30 attached to the reagent kit 100 used for measuring the sample by the sample measuring apparatus 300, and the second identification label 41 associated with the first identification information 31 recorded on the second identification label 40 attached to the reagent kit 100. Note that the first identification label 30 and the second identification label 40 may be attached to either the container 10 or the housing body 20, or may be housed in the housing body 20 together with the container 10.

When using the container 10, the user applies the first identification label 30 to the container 10, injects the sample into the container 10 to which the first identification label 30 is applied, and sets it in the sample measuring apparatus 300. The user also attaches the second identification label 40 to the recorded item of the subject information such as the chart 90.

When the container 10 is set by the user, the sample measuring apparatus 300 reads the first identification information 31 from the first identification label 30, and performs the measurement operation using the container 10. The sample measuring apparatus 300 generates the measurement result data 50 in which the first identification information 31 read from the first identification label 30 is associated with the measurement result 51 of the sample using the container 10. The measurement result data 50 includes at least the information of the measurement result 51 and the first identification information 31. The sample measuring apparatus 300 stores the measurement result data 50, or transmits the measurement result data to the server 600 that manages the measurement result 51. The sample measuring apparatus 300 may perform both of storing the measurement result data 50 and transmitting to the server 600. The measurement result data 50 is generated for every time a sample measurement using the container 10 is performed, and stored and recorded. The measurement result data 50 accumulated and recorded are mutually identified by the respective first identification information 31.

The terminal 500 handles the information of the subject from whom the sample was collected. The terminal 500 is, for example, a well-known tablet terminal, a portable information terminal such as a smartphone, a PC or other dedicated information terminal, and the like. The terminal 500 has a function of reading the second identification information 41 from the second identification label 40 by a camera, an optical scanner, a reading unit using short-range wireless communication, or the like.

The terminal 500 reads the second identification information 41 from the second identification label 40 attached to the medical record 90 by the user operation. Based on the second identification information 41 read from the second identification label 40, the terminal 500 stores the measurement result 51 in at least one of the sample measuring apparatus 300 or the server 600 that manages the measurement result 51, and specifies and acquires the measurement result data 50 including the first identification information 31 associated with the second identification information 41. That is, the terminal 500 transmits the second identification information 41 to the sample measuring apparatus 300 or the server 600, and requests the measurement result data 50 including the first identification information 31 associated with the second identification information 41. As a response to the request, the terminal 500 acquires the measurement result data 50 including the first identification information 31 associated with the second identification information 41 on a one-to-one basis. As a result, the subject information of the chart 90 to which the second identification label 40 is attached is associated with the measurement result 51 included in the acquired measurement result data 50.

In the second embodiment described above, the subject information and the information of the measurement result 51 of the subject can be associated with each other based on the identification information 41 and the first identification information 31 by the user attaching the second identification label 40 to the recorded item of the subject information such as the chart 90 or the like that can specify the subject from whom the sample was collected. In addition, it is not necessary for the user to manually input the subject information to the sample measuring apparatus every time the user performs a sample measurement, and the first identification information 31 given to the measurement result 51 and the second identification information 41 can be reliably associated. Also in the case of confirming the measurement result 51, it is possible to confirm the measurement result 51 which has the first identification information 31 associated with the second identification information 41 without manual input by using the second identification information 41. As a result, it is possible to easily suppress the erroneous input and associate the measurement result 51 with the subject information without using an integrated management system.

In the configuration example of FIG. 37, at least one of the first identification information 31 and the second identification information 41 includes information 71 for identifying the container 10. The information 71 for identifying the container 10 is, as described above, the container ID of the container 10 and the like. For example, both the first identification information 31 and the second identification information 41 may commonly include the container ID of the container 10. The terminal 500 acquires the information of the container 10 used for generating the measurement result 51 from the first identification information 31 or the second identification information 41 included in the measurement result data 50. In this way, not only the measurement result 51 and the subject information are associated by the first identification information 31, but also the container 10 used for generating the measurement result 51 is specified by the information 71 for identifying the container 10, such that it is possible to manage the individual containers 10 and the measurement results 51 thereof.

Figure 38:
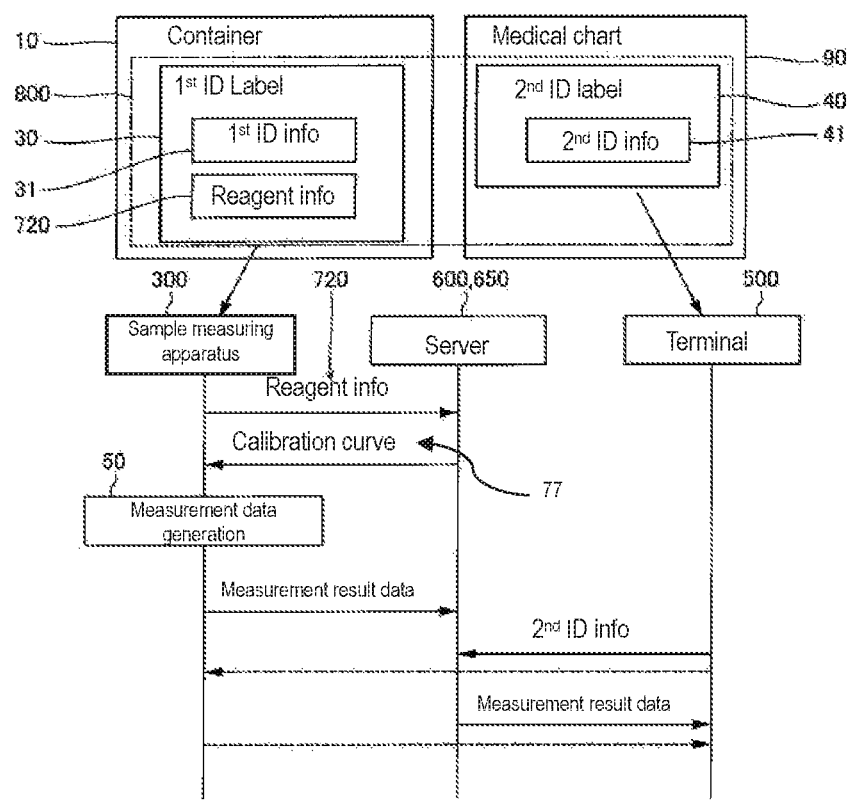
FIG. 38 is a diagram showing an example in which a data structure includes information on reagents.

In the example of FIG. 38, the first identification information 31 includes information 720 on the reagent contained in the container 10. The information of the reagent is, for example, the lot number of the reagent, as described above.

The sample measuring apparatus 300 acquires information of the calibration curve 77 for measuring the measurement result of the sample using the reagent from the server 650 that manages the reagent information based on the reagent information 720 contained in the container 10. In FIG. 38, for convenience of illustration, the server 600 that manages the measurement result data 50 and the server 650 that manages the reagent information are collectively illustrated; however, the server 650 that manages the reagent information and the measurement result and the server 600 that manages the data 50 may be separate and independent servers.

The sample measuring apparatus 300 reads the reagent information 720 together with the first identification information 31 from the first identification label 30, and performs the measurement operation using the container 10. The sample measuring apparatus 300 transmits the reagent information 720 to the server 650, requests transmission of the calibration curve 77 corresponding to the reagent information 720, and acquires the information on the calibration curve 77 as a response to the request. The sample measuring apparatus 300 measures the measurement result using the acquired calibration curve 77.

In this way, in the configuration of FIG. 38, the information on the calibration curve 77 can be specified based on the reagent information 720 contained in the container 10, and acquired from the server 650 managing the reagent information. As a result, an appropriate measurement result can be obtained without preparing a calibration curve for measurement. The calibration curve 77 can be slightly changed depending on the elapsed period of time after the preparation of the reagent; therefore, in the configuration in which the calibration curve 77 is acquired from the server 650 that manages the reagent information, it is possible to improve the measurement accuracy since the information on the calibration curve 77 can also be updated through the network 710.

Figure 39:
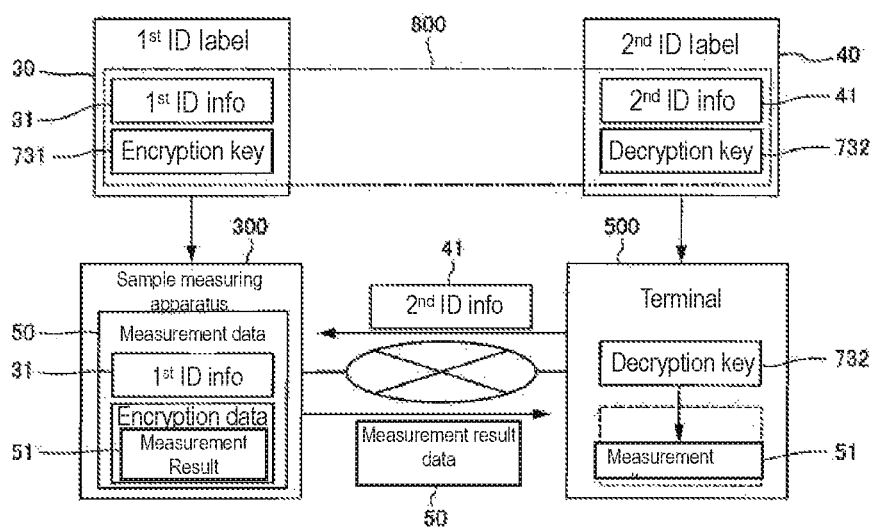
FIG. 39 is a diagram showing an example in which a data structure has encryption and decryption key information.
Figure 40:
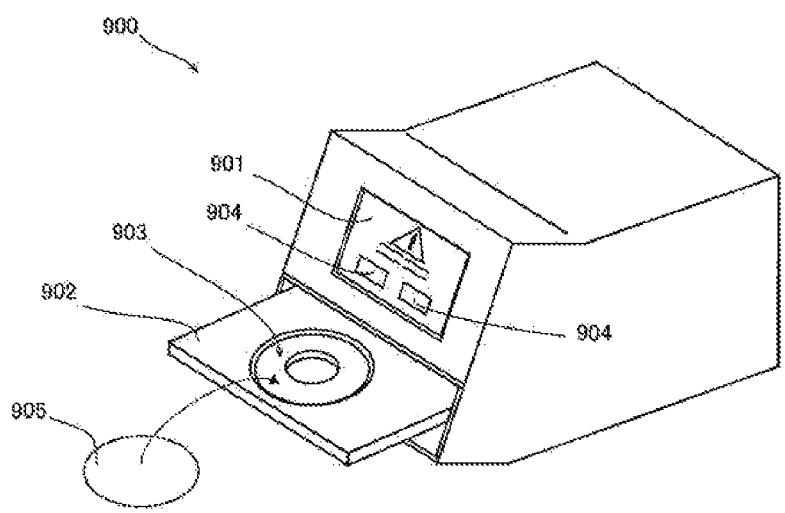
FIG. 40 is a diagram for describing the conventional art.

In the configuration example of FIG. 39, the first identification label 30 includes the encryption key 731 for encrypting the measurement result 51, and the decryption key 732 for decrypting the measurement result 51 obtained by encrypting the second identification label 40. The encryption key 731 is, for example, a public key of a public key encryption method, and the decryption key 732 may be a secret key that decrypts information encrypted with a public key.

When generating the measurement result data 50, the sample measuring apparatus 300 encrypts the measurement result 51 using the encryption key 731 read from the first identification label 30. The measurement result data 50 includes the first identification information 31 and the encrypted measurement result 51. In this way the measurement result 51 is encrypted, and it cannot be read without the decryption key 732.

The terminal 500 specifies and acquires the measurement result data 50 including the first identification information 31 associated with the second identification information 41 based on the second identification information 41 read from the second identification label 40. Then, the terminal 500 decrypts the encrypted measurement result 51 using the decryption key 732 read from the second identification label 40. As a result, the measurement result 51 can be viewed in the terminal 500. Since the second identification label 40 is given to the medical chart 90 of the subject and managed by the user, it can be managed only by the user. As a result, reading by a third party can be prevented even when the measurement result data 50 is transmitted and received via the network 710.

Note that the embodiments disclosed herein are examples in all respects and are not restrictive. The scope of the present invention is indicated not by the description of the above embodiments but by the scope of the claims, and includes meanings equivalences to the claims and all modification within the scope of the claims.

What is claimed is:

1. A method of associating measurement results comprising:
    measuring a sample;
    providing a first identification label including a first identification information on a container configured to hold the sample;
    reading the first identification label to acquire the first identification information by a sample measuring apparatus;
    associating the first identification information read from the first identification label with a measurement result of the sample; and
    physically attaching a separate second identification label including second identification information corresponding to the first identification information to a recorded item of subject information, wherein the recorded item of subject information comprises a physical medical record or chart that is different from the container,
    wherein the second identification information comprises information used to verify a correspondence of the second identification information to the first identification information.

2. The method according to claim 1, wherein the first identification label includes an information relating to measurement using the container.

3. The method according to claim 2, wherein the information relating to measurement using the container includes at least one of a measurement condition, a measurement item, and a calibration curve.

4. The method according to claim 1, wherein the second identification information includes the same or corresponding information as the first identification information.

5. The method according to claim 4, wherein the second identification information includes the same encrypted information as the first identification information.

6. The method according to claim 4, wherein the first identification information includes an information obtained by converting the second identification information by a predetermined process.

7. The method according to claim 1, further comprising:
accommodating a container in a housing body, wherein the container is used for measuring a sample by a sample measuring apparatus and has a housing part for containing a reagent that reacts with the sample.

8. The method according to claim 7, wherein
providing the first identification label on the container, or housed within the housing body together with the container.

9. The method according to claim 7, wherein
providing the second identification label on either the container or the housing body, or housed within the housing body together with the container.

10. The method according to claim 7, wherein
the second identification label is a label affixed to at least one of the container or housing body.

11. The method according to claim 10, wherein
providing the second identification label so as to overlap the first identification label in a state where the second identification label is peelable from the first identification label.

12. The method according to claim 1, further comprising:
accommodating the container in a housing body, wherein the container is used for measuring a sample by a sample measuring apparatus;
wherein the first identification label and the second identification label are attached to the container.

13. The method according to claim 1, wherein
the first identification label and the second identification label are both attached to the container.

14. The method according to claim 1, further comprising:
accommodating the container in a housing body, wherein the container is used for measuring a sample by a sample measuring apparatus;
wherein the first identification label is attached to the container; and
the second identification label is attached to the housing body.

15. The method according to claim 1, further comprising:
accommodating the container in a housing body, wherein the container is used for measuring a sample by a sample measuring apparatus;
wherein an unseal position of the housing body is regulated;
providing the second identification label on the housing body so as to overlap the unseal position; and
unsealing the housing body by separating the second identification label from the housing body in accordance with opening the housing body, or by separating the second identification label from the housing body.

16. The method according to claim 1, wherein
the first identification information includes an information for identifying the container.

17. The method according to claim 1, wherein
the first identification information and the second identification information include a container identification for identifying the container.

18. A method of associating measurement results comprising:
measuring a sample;
providing a first identification label including a first identification information on a container configured to hold the sample;
reading the first identification label to acquire the first identification information by a sample measuring apparatus;
associating the first identification information read from the first identification label with a measurement result of the sample;
physically attaching a separate second identification label including second identification information associated with the first identification information to a recorded item of subject information, wherein the recorded item of subject information comprises a physical document that is different from the container; and
providing a separate third identification label with a housing body for accommodating the container, wherein the second identification label and the third identification label together are configured to determine whether the housing body is sealed or unsealed.

* * * * *